United States Patent
Feain et al.

(10) Patent No.: US 11,295,449 B2
(45) Date of Patent: Apr. 5, 2022

(54) THREE-DIMENSIONAL TRACKING OF A TARGET IN A BODY

(71) Applicant: ASTO CT, INC., Madison, WI (US)

(72) Inventors: Ilana Feain, New South Wales (AU); Chun-Chien Shieh, New South Wales (AU); Michelle Dunbar, New South Wales (AU)

(73) Assignee: ASTO CT, INC., Madison, WI (US)

(*) Notice: Subject to any disclaimer, the term of this patent is extended or adjusted under 35 U.S.C. 154(b) by 379 days.

(21) Appl. No.: 16/763,255

(22) PCT Filed: Nov. 16, 2017

(86) PCT No.: PCT/AU2017/051261
§ 371 (c)(1),
(2) Date: May 12, 2020

(87) PCT Pub. No.: WO2018/090091
PCT Pub. Date: May 24, 2018

(65) Prior Publication Data
US 2021/0174511 A1     Jun. 10, 2021

(30) Foreign Application Priority Data
Nov. 16, 2017 (AU) ................................ 2016904747

(51) Int. Cl.
*G06K 9/00*     (2006.01)
*G06T 7/00*     (2017.01)
(Continued)

(52) U.S. Cl.
CPC .......... *G06T 7/0016* (2013.01); *G06K 9/6202* (2013.01); *G06K 9/6296* (2013.01);
(Continued)

(58) Field of Classification Search
CPC ......... G06T 7/0016; G06T 7/277; G06T 7/75; G06T 2207/10076; G06T 2207/10116;
(Continued)

(56) References Cited

U.S. PATENT DOCUMENTS 7,894,649 B2   2/2011   Fu et al.
7,894,664 B2   2/2011   Kerwin et al.
(Continued)

FOREIGN PATENT DOCUMENTS

CN            101076282     11/2007
WO   WO 2015125600 A1   8/2015
(Continued)

OTHER PUBLICATIONS

Barnes et al., Dosimetric evaluation of lung tumor immobilization using breath hold at deep inspiration. Int J Radiat Oncol Biol Phys. 2001, 50: 1091-1098.
(Continued)

*Primary Examiner* — Atiba O Fitzpatrick
(74) *Attorney, Agent, or Firm* — Casimir Jones, S.C.; Thomas A. Isenbarger

(57) ABSTRACT

Disclosed is a method and system for three-dimensional tracking of a target located within a body, the method performed using at least one processing system. A two-dimensional scanned image of the body including the target is processed to obtain a two-dimensional image of the target. A first present dataset of the target is predicted using a previous dataset of the target and a state transition model, the first present dataset includes a three-dimensional present position value of the target. A second present dataset of the target is measured by template-matching of the two-dimensional image of the target with a model of the target. A third present dataset of the target is estimated by statistical inference using the first present dataset and the second
(Continued)

present dataset. The previous dataset of the target is updated to match the third present dataset.

20 Claims, 12 Drawing Sheets

(51) Int. Cl.
  *G06T 7/277* (2017.01)
  *G06T 7/73* (2017.01)
  *G06K 9/62* (2022.01)

(52) U.S. Cl.
  CPC .............. *G06T 7/277* (2017.01); *G06T 7/75* (2017.01); *G06T 2207/10076* (2013.01); *G06T 2207/10116* (2013.01); *G06T 2207/30061* (2013.01); *G06T 2207/30096* (2013.01)

(58) Field of Classification Search
  CPC   G06T 2207/30061; G06T 2207/30096; G06K 9/6202; G06K 9/6296
  See application file for complete search history.

(56) References Cited

U.S. PATENT DOCUMENTS

| | | | |
|---|---|---|---|
| 8,239,005 | B2 | 8/2012 | Wright et al. |
| 8,363,953 | B2 | 1/2013 | Kameyama et al. |
| 8,460,166 | B2 | 6/2013 | Guckenburger et al. |
| 8,824,762 | B2 | 9/2014 | Rivaz et al. |
| 9,105,095 | B2 | 8/2015 | Maizeroi-Eugene et al. |
| 2006/0251304 | A1* | 11/2006 | Florin .................. G06T 7/12 382/128 |
| 2009/0161933 | A1 | 6/2009 | Chen |
| 2014/0050297 | A1 | 2/2014 | Mostafavi |
| 2014/0333783 | A1* | 11/2014 | LaFarelle ............ G01C 11/025 348/208.1 |
| 2014/0334686 | A1* | 11/2014 | LaFarelle ............... G06T 7/246 382/107 |
| 2014/0334705 | A1 | 11/2014 | Ishii et al. |
| 2015/0073765 | A1 | 3/2015 | Boettger et al. |
| 2015/0279031 | A1 | 10/2015 | Cavusoglu et al. |
| 2015/0314138 | A1 | 11/2015 | Maurer et al. |
| 2016/0047657 | A1* | 2/2016 | Caylor ................. G05D 1/0088 701/521 |
| 2016/0379074 | A1* | 12/2016 | Nielsen ................. H04N 7/181 348/143 |
| 2018/0279921 | A1* | 10/2018 | Datta .................... G06K 9/6247 |

FOREIGN PATENT DOCUMENTS

| | | |
|---|---|---|
| WO | WO 2016141416 A1 | 9/2016 |
| WO | WO 2018090091 A1 | 5/2018 |

OTHER PUBLICATIONS

Bryant et al., Registration of clinical volumes to beams-eye-view images for real-time tracking. Med Phys. Dec. 2014;41(12):121703.
Chen, et al., Prior image constrained compressed sensing (PICCS): a method to accurately reconstruct dynamic CT images from highly undersampled projection data sets. Med Phys. Feb. 2008;35(2):660-3.
Cootes et al., The use of active shape models for locating structures in medical images, 1993, Information Processing in Medical Imaging, Lecture Notes in Computer Science, vol. 687, pp. 33-47.
Depuydt et al., Treating patients with real-time tumor tracking using the Vero gimbaled linac system: implementation and first review. Radiother Oncol. Sep. 2014;112(3):343-51.
Descovich et al., Characteristics of megavoltage cone-beam digital tomosynthesis. Med Phys. Apr. 2008;35(4):1310-6.
Dobbins III et al., Digital x-ray tomosynthesis: current state of the art and clinical potential. Phys Med Biol. Sep. 2003; 48(19) R65.
Fletcher-Heath et al., Automatic segmentation of non-enhancing brain tumors in magnetic resonance images. Artif Intell Med. Jan.-Mar. 2001;21(1-3):43-63.
Furtado et al., Real-time 2D/3D registration using kV-MV image pairs for tumor motion tracking in image guided radiotherapy. Acta Oncol. Oct. 2013;52(7):1464-71.
Gendrin et al., Monitoring tumor motion by real time 2D/3D registration during radiotherapy. Radiother Oncol. Feb. 2012;102(2):274-80.
George et al., On the accuracy of a moving average algorithm for target tracking during radiation therapy treatment delivery. Med Phys. Jun. 2008;35(6):2356-65.
Godfrey et al, Digital tomosynthesis with an on-board kilovoltage imaging device. Int J Radiat Oncol Biol Phys. May 1, 2006;65(1):8-15.
Guckenberger et al., Intra-fractional uncertainties in cone-beam CT based image-guided radiotherapy (IGRT) of pulmonary tumors. Radiother Oncol. Apr. 2007;83(1):57-64.
Hardcastle et al., (2016), MO-FG-BRA-06: Electromagnetic Beacon Insertion in Lung Cancer Patients and Resultant Surrogacy Errors for Dynamic MLC Tumour Tracking. Med. Phys., 43: 3710-3711.
Hong et al., Migration of implanted markers for image-guided lung tumor stereotactic ablative radiotherapy. J Appl Clin Med Phys. Mar. 4, 2013;14(2):4046: 77-89.
Hugo et al., Marker-free lung tumor trajectory estimation from a cone beam CT sinogram. Phys Med Biol. May 7, 2010;55(9):2637-50.
IEC 61217: Radiotherapy Equipment-Coordinates, Movements and Scales 2011 Technical Report International Electrotechnical Commission.
Imura et al., Insertion and fixation of fiducial markers for setup and tracking of lung tumors in radiotherapy. Int J Radiat Oncol Biol Phys. Dec. 1, 2005;63(5):1442-7.
International Search Report and Written Opinion for Application No. PCT/AU2017/051261 dated Feb. 27, 2018, 10 pages.
International Search Report and Written Opinion for Application No. PCT/AU2016/000086 dated May 16, 2016, 14 pages.
Johnson et al., The ITK Software Guide: Design and Functionality, 4th edn, Kitware Inc., 2015.
Kavanagh et al., Obtaining breathing patterns from any sequential thoracic x-ray image set. Phys Med Biol. Aug. 21, 2009;54(16):4879-88.
Keall et al., The management of respiratory motion in radiation oncology report of AAPM Task Group 76. Med Phys. Oct. 2006;33(10):3874-900.
Kirschner, The Probabilistic Active Shape Model: From Model Construction to Flexible Medical Image Segmentation, 2013, Technische Universitat, Darmstadt, Ph. D. Thesis, 209 pages.
Kothary et al., Safety and efficacy of percutaneous fiducial marker implantation for image-guided radiation therapy. J Vasc Interv Radiol. Feb. 2009;20(2):235-9.
Kupelian et al., Multi-institutional clinical experience with the Calypso System in localization and continuous, real-time monitoring of the prostate gland during external radiotherapy, 2007 Int. J. Radiat. Oncol. 67 1088-98.
Lewis et al., Markerless lung tumor tracking and trajectory reconstruction using rotational cone-beam projections: a feasibility study. Phys Med Biol. May 7, 2010;55(9):2505-22.
Low et al, A novel CT acquisition and analysis technique for breathing motion modeling. Phys Med Biol. Jun. 7, 2013;58(11):L31-6.
Lu et al., An integrated approach to segmentation and nongrid registration for application in image-guided pelvic radiotherapy, 2011, Medical Image Analysis, vol. 15, Issue 5, pp. 772-785.
Lightsabr, Lung Cancer Radiotherapy Using Realtime Dynamic Multileaf Collimator (MLC) Adaptation and Radiofrequency Tracking Clinical trial NCT02514512 https://clinicaltrials.gov/ct2/show/NCT02514512.
Mattes et al., Nonrigid multimodality image registration, Proc. SPIE 4322, Medical Imaging 2001.
Maurer et al., On-board four-dimensional digital tomosynthesis: first experimental results. Med Phys. Aug. 2008;35(8):3574-83.

(56) References Cited

OTHER PUBLICATIONS

Poulsen et al., A method to estimate mean position, motion magnitude, motion correlation, and trajectory of a tumor from cone-beam CT projections for image-guided radiotherapy. Int J Radiat Oncol Biol Phys. Dec. 1, 2008;72(5):1587-96.
Poulsen et al., A method for robust segmentation of arbitrarily shaped radiopaque structures in cone-beam CT projections. Med Phys. Apr. 2011;38(4):2151-6.
Ren et al., A novel digital tomosynthesis (DTS) reconstruction method using a deformation field map. Med Phys. Jul. 2008;35(7):3110-5.
Ren et al., A limited-angle intrafraction verification (LIVE) system for radiation therapy. Med Phys. Feb. 2014;41(2):020701-01-020701-09.
Richter et al., Feasibility study for markerless tracking of lung tumors in stereotactic body radiotherapy. Int J Radiat Oncol Biol Phys. Oct. 1, 2010;78(2):618-27.
Rit et al., The Reconstruction Toolkit (RTK), an open-source cone-beam CT reconstruction toolkit based on the Insight Toolkit (ITK) J. Phys.: Conf. Ser. 489(1), 012079-012079 2014.
Roman et al., Interfractional Positional Variability of Fiducial Markers and Primary Tumors in Locally Advanced Non-Small-Cell Lung Cancer During Audiovisual Biofeedback Radiotherapy, 2012 Int J Radiation Oncol Biol Phys. 83(5)1566-72.
Rottmann et al., Markerless EPID image guided dynamic multi-leaf collimator tracking for lung tumors. Phys Med Biol. Jun. 21, 2013;58(12):4195-204.
Ruan, et al. Real-time profiling of respiratory motion: baseline drift, frequency variation and fundamental pattern change. Phys Med Biol. Aug. 7, 2009;54(15):4777-92.
Santoro et al., Evaluation of respiration-correlated digital tomosynthesis in lung. Med Phys. Mar. 2010;37(3):1237-45.
Seco et al., Dosimetric impact of motion in free-breathing and gated lung radiotherapy: a 4D Monte Carlo study of intrafraction and interfraction effects. Med Phys. Jan. 2008;35(1):356-66.
Schmidt et al., Clinical use of iterative 4D-cone beam computed tomography reconstructions to investigate respiratory tumor motion in lung cancer patients, (2014) Acta Oncologica, 53:8, 1107-1113.
Seiler et al., A novel tracking technique for the continuous precise measurement of tumour positions in conformal radiotherapy. Phys Med Biol. Sep. 2000;45(9):N103-10.
Serpa et al., Suitability of markerless EPID tracking for tumor position verification in gated radiotherapy. Med Phys. Mar. 2014;41(3):031702-01-031702-13.
Shah et al., Intrafraction variation of mean tumor position during image-guided hypofractionated stereotactic body radiotherapy for lung cancer. Int J Radiat Oncol Biol Phys. Apr. 1, 2012;82(5):1636-41.
Sharp et al., Tracking errors in a prototype real-time tumour tracking system. Phys Med Biol. Dec. 7, 2004;49(23):5347-56.
Shieh et al., Markerless tumor tracking using short kilovoltage imaging arcs for lung image-guided radiotherapy. Phys Med Biol. Dec. 21, 2015;60(24):9437-54.
Shieh et al., Improving thoracic four-dimensional cone-beam CT reconstruction with anatomical-adaptive image regularization (AAIR). Phys Med Biol. Jan. 21, 2015;60(2):841-68.
Sonke et al., Frameless stereotactic body radiotherapy for lung cancer using four-dimensional cone beam CT guidance. Int J Radiat Oncol Biol Phys. Jun. 1, 2009;74(2):567-74.
Stevens et al., Respiratory-driven lung tumor motion is independent of tumor size, tumor location, and pulmonary function. Int J Radiat Oncol Biol Phys. Sep. 1, 2001;51(1):62-8.
Tang et al. Fluoroscopic tracking of multiple implanted fiducial markers using multiple object tracking. Phys Med Biol. Jul. 21, 2007;52(14):4081-98.
Teske et al., Real-time markerless lung tumor tracking in fluoroscopic video: Handling overlapping of projected structures. Med Phys. May 2015;42(5):2540-9.
Trofimov et al., Tumor trailing strategy for intensity-modulated radiation therapy of moving targets. Med Phys. May 2008;35(5):1718-33.
Van Der Reijden et al., Motion compensated digital tomosynthesis. Radiother Oncol. Dec. 2013;109(3):398-403.
Van Der Voort Van Zyp et al., Stability of markers used for real-time tumor tracking after percutaneous intrapulmonary placement. Int J Radiat Oncol Biol Phys. Nov. 1, 2011;81(3):e75-81.
Van Sornsen De Koste et al., Digital tomosynthesis (DTS) for verification of target position in early stage lung cancer patients. Med Phys. Sep. 2013;40(9):091904.
Van Sornsen De Koste et al., Markerless tracking of small lung tumors for stereotactic radiotherapy. Med Phys. Apr. 2015;42(4):1640-52.
Willoughby et al., Target localization and real-time tracking using the Calypso 4D localization system in patients with localized prostate cancer. Int J Radiat Oncol Biol Phys. Jun. 1, 2006;65(2):528-34.
Yang et al., A novel markerless technique to evaluate daily lung tumor motion based on conventional cone-beam CT projection data. Int J Radiat Oncol Biol Phys. Apr. 1, 2012;82(5):e749-56.
Zacharaki et al., ORBIT: a multiresolution framework for deformable registration of brain tumor images. IEEE Trans Med Imaging. Aug. 2008;27(8):1003-17.
Zhang et al., A technique for estimating 4D-CBCT using prior knowledge and limited-angle projections. Med Phys. Dec. 2013;40(12):121701-01-121701-16.
AU Examination Report for corresponding App No. 2016228944, dated Oct. 29, 2019, 5 pages.
EP Search Report for corresponding App. No. 16760919.7, dated Apr. 8, 2020 5 pages.
Extended EP Search Report for corresponding App. No. 17871787.2, dated Jun. 2, 2021, 4 pages.
Office Action issued for corresponding CN Application No. 201680015346.6, dated Feb. 25, 2021, 11 pages.

* cited by examiner

THREE-DIMENSIONAL TRACKING OF A TARGET IN A BODY

TECHNICAL FIELD

The present invention generally relates to a system and/or a method or process for tracking a target, and more specifically to a system and/or a method or process for three-dimensional tracking of a target located within a body. In further specific examples, a system and/or a method or process is formed or provided for markerless tracking of a target in three dimensions, using two-dimensional images of the target.

BACKGROUND

Lung tumour motions are clinically significant and unpredictable. During lung cancer radiotherapy, tumour motion is a major challenge to accurate beam targeting of tumours. There is currently no technology able to directly track tumour motion in three dimensions during treatment.

Current motion management techniques rely on pre-treatment imaging technologies such as four-dimensional computed tomography (4D-CT) and four-dimensional cone-beam computed tomography (4D-CBCT), which may not actually represent the actual tumour motion during treatment. 4D-CT-based margins have been known to underestimate lung tumour motion and to lead to significant tumour underdose for lung proton therapy.

Current real-time tumour tracking technologies rely on the implantation of radiopaque fiducial markers or electromagnetic transponder beacons. However, marker or beacon implantation is an invasive and costly procedure that is not widely available. Marker-induced toxicity and surrogacy errors are also common problems.

Markerless tumour tracking methods have been proposed using kilovoltage (kV) and megavoltage (MV) imaging. A major challenge of markerless tumour tracking is that tumours are rarely consistently visible on kV or MV projections due to obstruction by surrounding anatomic structures and changes in radiological depth due to gantry rotation. Obstruction by the treatment beam aperture in intensity-modulated radiation therapy (IMRT) treatments is also a common problem for MV-based methods.

Presently, there is insufficient tumour visibility for tracking tumours in patients using the anterior-posterior (AP) view. Other views have larger radiological depths and are generally more challenging for tracking than the AP view. Consequently, more patients are expected to be ineligible for markerless tracking during gantry rotation. Another limitation is the lack of ground truth for evaluating the accuracy of markerless tumour tracking on clinical data. Most published studies validated their tracking results by correlating the tracked trajectories with surrogate signals (e.g. abdominal or diaphragm motion) or comparing with subjective measurements of tumour positions (e.g. visual inspection and manual segmentation).

Additional limitations of X-ray imaging techniques include the fact that X-ray imaging only provides two-dimensional (2D) imaging information. Motion information parallel to the X-ray beam path is not available. For this reason, tumour tracking using X-ray imaging suffers from large tracking uncertainties.

There is a need for new or improved systems for tracking tumour motions and/or methods or processes of tracking tumour motions.

The reference in this specification to any prior publication (or information derived from the prior publication), or to any matter which is known, is not, and should not be taken as an acknowledgment or admission or any form of suggestion that the prior publication (or information derived from the prior publication) or known matter forms part of the common general knowledge in the field of endeavour to which this specification relates.

SUMMARY

This Summary is provided to introduce a selection of concepts in a simplified form that are further described below in the Preferred Embodiments. This Summary is not intended to identify key features or essential features of the claimed subject matter, nor is it intended to be used to limit the scope of the claimed subject matter.

According to one example aspect, there is provided a method for three-dimensional tracking of a target located within a body, the method performed by at least one processing system, and comprising the steps of: processing a two-dimensional scanned image of the body including the target to obtain a two-dimensional image of the target, wherein the two-dimensional scanned image is acquired from a scanning device; predicting a first present dataset of the target by using a previous dataset of the target and a state transition model, wherein the first present dataset includes at least a three-dimensional present position value of the target, and wherein the previous dataset includes at least a three-dimensional previous position value of the target; measuring a second present dataset of the target by template-matching of the two-dimensional image of the target with a model of the target, wherein the second present dataset includes at least a two-dimensional present position value of the target; estimating a third present dataset of the target by statistical inference using the first present dataset and the second present dataset, wherein the third present dataset includes at least a three-dimensional present position value of the target; and updating the previous dataset of the target to match the third present dataset.

According to another example aspect, there is provided a system for three-dimensional tracking of a target located within a body, comprising: a scanning device configured to acquire a two-dimensional scanned image of the body including the target; and a processing system configured to: receive and process the two-dimensional scanned image of the body including the target to obtain a two-dimensional image of the target; predict a first present dataset of the target by using a previous dataset of the target and a state transition model, wherein the first present dataset includes at least a three-dimensional present position value of the target, and wherein the previous dataset includes at least a three-dimensional previous position value of the target; measure a second present dataset of the target by template-matching of the two-dimensional image of the target with a model of the target, wherein the second present dataset includes at least a two-dimensional present position value of the target; estimate a third present dataset of the target by statistical inference using the first present dataset and the second present dataset, wherein the third present dataset includes at least a three-dimensional present position value of the target; and update the previous dataset of the target to match the third present dataset.

BRIEF DESCRIPTION OF FIGURES

Example embodiments are apparent from the following description, which is given by way of example only, of at least one preferred but non-limiting embodiment, described in connection with the accompanying figures.

PREFERRED EMBODIMENTS

Figure 1:
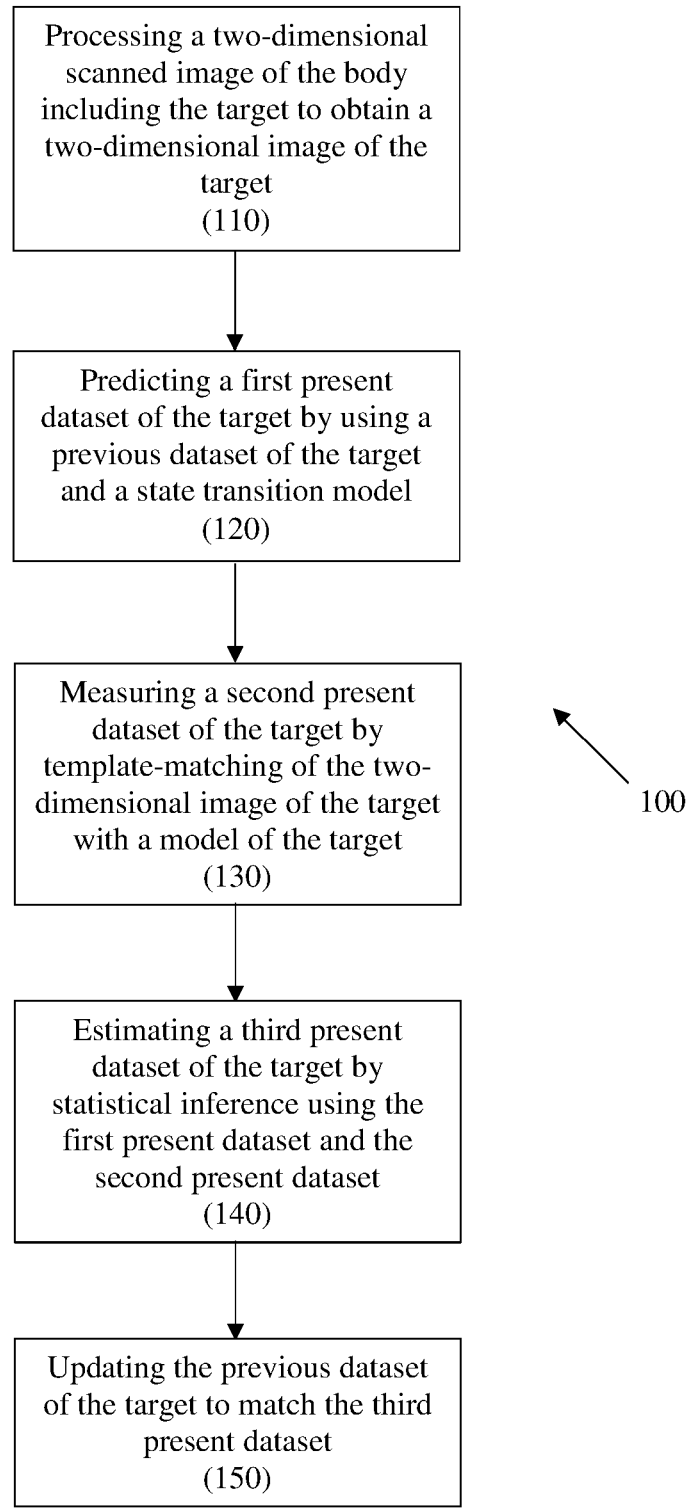
FIG. 1 illustrates an example method for three-dimensional tracking of a target located within a body.

The following modes, given by way of example only, are described in order to provide a more precise understanding of the subject matter of a preferred embodiment or embodiments. In the figures, incorporated to illustrate features of an example embodiment, like reference numerals are used to identify like parts throughout the figures.

In one broad form, there is provided a method for tracking a target located within a body. The method includes acquiring a model of the target and a model of the body anatomy excluding the target. Then, acquiring a projected image of the target. Then, predicting a first present dataset of the target by using a previous dataset of the target and a state transition model. The method further includes measuring a second present dataset of the target by template-matching of the projected image with the model of the target. Then, estimating a third present dataset of the target by statistical inference using the first present dataset and the second present dataset. Then, updating the previous dataset. Each dataset of the target (i.e. first, second, and third) includes a position value and a measure of the uncertainty of the position value of the target.

Referring to FIG. 1, there is illustrated an example method 100 for three-dimensional tracking of a target located within a body, method 100 being performed by at least one processing system. Method 100 includes step 110 of processing a two-dimensional scanned image of the body including the target to obtain a two-dimensional image of the target, wherein the two-dimensional scanned image is acquired from a scanning device. At step 120, predicting a first present dataset of the target by using a previous dataset of the target and a state transition model, wherein the first present dataset includes at least a three-dimensional present position value of the target, and wherein the previous dataset includes at least a three-dimensional previous position value of the target. At step 130, measuring a second present dataset of the target by template-matching of the two-dimensional image of the target with a model of the target, wherein the second present dataset includes at least a two-dimensional present position value of the target. At step 140, estimating a third present dataset of the target by statistical inference using the first present dataset and the second present dataset, wherein the third present dataset includes at least a three-dimensional present position value of the target. Then, at step 150, updating the previous dataset of the target to match the third present dataset.

An example of a target is a tumour. Other examples of a target include an abnormal growth of tissue, a biological organ, or biological tissue. An example of a body is a human body. Another example of a body is an animal body.

In some examples, the steps of method 100 are executed sequentially. In some examples, at least some steps of method 100 are executed in parallel.

A dataset of the target describes a state of the target, which may include information on the position of the target and may further include statistical information on the position of the target. For example, the dataset may comprise a position value and a covariance value as a measure of the uncertainty of the position value. The statistical information may be obtained from present or past tracking information, present or past measurements, and/or any other knowledge on the nature of the target and of the tracking process/measurement system (e.g. random and/or systematic errors of the measurement system).

In some examples, each dataset (i.e. first, second, and third datasets) further includes a measure of an uncertainty in the respective position value of the target (i.e. the two- or three-dimensional position value included in the dataset).

Preferably, though not necessarily, the position value in a dataset of the target refers to a centroid position of the target. The position value may be relative to the body, or relative to a portion of the body, or relative to some other coordinate system defined with reference to any point internal or external to the body.

In some examples, the statistical inference utilises Bayesian probability, or a Bayesian probability approach. In some examples, the statistical inference utilises an extended Kalman filter, or an extended Kalman filter approach.

Preferably, though not necessarily, method 100 implements a Bayesian framework based on the extended Kalman filter. The Kalman filter, as well as its extended version, is a statistical inference approach for updating a state variable and the covariance matrix of its distribution, by combining a prediction and a measurement of the state variable. The measurement of the state variable contains some inherent uncertainty (e.g. due to noise or due to physical limitations).

In some example embodiments of method 100, the target is tracked in three-dimensional (3D) space. In such examples, the state variable, x, represents the 3D position of the target centroid, and the covariance matrix, P, describes the distribution of the target position in 3D space. Since step 130 is effectively measuring a two-dimensional position of the target from a two-dimensional image of the target, method 100 requires extrapolation of the target's position in 3D space from a 2D image. The power of a Kalman filter for statistical inference in step 140 is that covariance matrix P exploits both the uncertainties and the correlations of each motion component, making it possible to estimate the 3D position of the target based on a 2D measurement.

In some examples, the target is a surrogate object, such as a radiopaque marker or a beacon implanted in a human body. In other examples, the target is a soft tissue target. In some examples, the target is a tumour. In some examples, the target is a lung tumour, moving due to a patient's breathing pattern.

Tracking of a moving target (such as a lung tumour) may require repeated execution of certain steps of method 100. In some examples, acquisition of a two-dimensional scanned image is repeated, or continuously executed, at multiple points in time, and steps 110, 120, 130, 140, and 150 are executed after each acquisition of the two-dimensional scanned image, to continuously track the target's position. In some examples, tracking occurs in real time, for example, during treatment such as a radiotherapy session.

Method 100 may further include a step of adjusting an apparatus operating on, or interacting with, the target in response to the third present dataset. In some examples where the target is a tumour, the apparatus may be a treatment apparatus, such as a radiation source for radiotherapy, or a patient table. This apparatus should be adjusted (e.g. by varying the direction of a radiation beam) in response to the motion of the tumour. The third present dataset estimated by method 100 provides information on such motion. Therefore, the apparatus may be adjusted (either manually or automatically) following each execution of method 100, as the position of the target is tracked.

Figure 2:
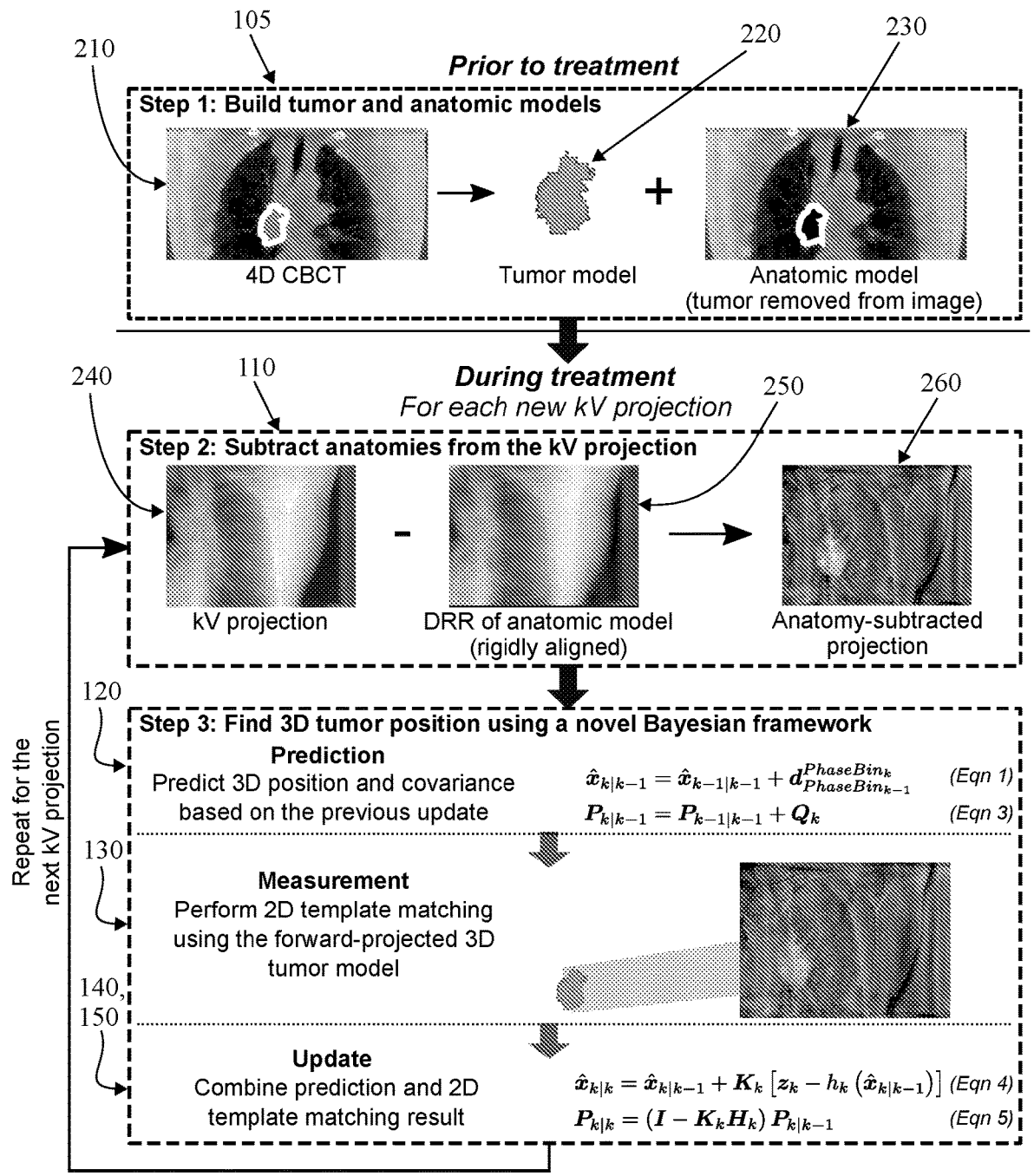
FIG. 2 illustrates an example implementation of the method of FIG. 1, where the target is a lung tumour.

Referring to FIG. 2, there is illustrated an example embodiment of method 100 where the target is a lung tumour. FIG. 2 further illustrates additional step 105, of acquiring a model of the target and a model of the body anatomy excluding the target. In some examples, step 105 may be computationally intensive and as such, it is advantageous that it not be repeated prior to each iteration of method 100. In some examples, step 105 is executed once for each patient, before commencement of a treatment. The acquired models of the target and of the body anatomy can then be stored on a processing system, or any memory device. Execution of method 100 may then commence, with the models of the target and of the body anatomy being accessed as required during execution of method 100.

The model of the target and/or the model of the body anatomy provide information of the spatial distribution, or location, of the target and of the body anatomy at one or more points in time, or at one or more instances in a time period. The time period may span one or more cycles of a physiological process, such as a respiratory cycle. Preferably, though not necessarily, the spatial distribution information provided by the models is 3D spatial distribution information. The model of the body anatomy may provide information (e.g. location, distribution, arrangement, and motion information) on the internal structure and components of the body that contains the target.

In some examples, the model of the target and/or the model of the body anatomy is any one of, or a combination of: a physical model, a scientific model, a 3D model, and a computer model. The model of the target and/or the model of the body anatomy may include one or more vectors, matrices, and/or data structures.

In one example, the model of the target and/or the model of the body anatomy are derived, or built, from one or more images. These images may be acquired prior to a treatment (e.g. radiation treatment) and are therefore referred to as "prior images".

In some examples, the model of the target is derived from prior images and from a surrogate signal. The surrogate signal may be indicative of a motion of the body and/or of the target. The surrogate signal may be used to augment, or enhance, the model of the target by providing further information on the target's motion. The surrogate signal may be provided, or emitted, from a beacon or probe located internally or externally to the body. In some examples, the surrogate signal tracks an external motion of the body. In some examples, the surrogate signal is estimated, detected, or measured from the projected image. The surrogate signal may be emitted by a surrogate object, such as a radiopaque marker or a beacon implanted in the body. In some examples, method 100 further comprises a step of implanting a surrogate object in the body prior to acquiring the 2D scanned image (i.e. prior to step 110).

In one example, the prior images are 3D images. In another example, the prior images are 3D diagnostic images of a patient. In another example, the prior images span different points in time such that their subject is illustrated in each prior image at a different point in time. In a preferred example, the prior images are four-dimensional cone beam computed tomography (4D-CBCT) images.

In some examples, the prior images are X-ray images. The prior images preferably illustrate the target and its neighbouring region within the body (including anatomical features of the neighbouring regions within the body). A high-quality prior image is significant as it provides knowledge of how the target can be differentiated from surrounding objects.

Figure 3:
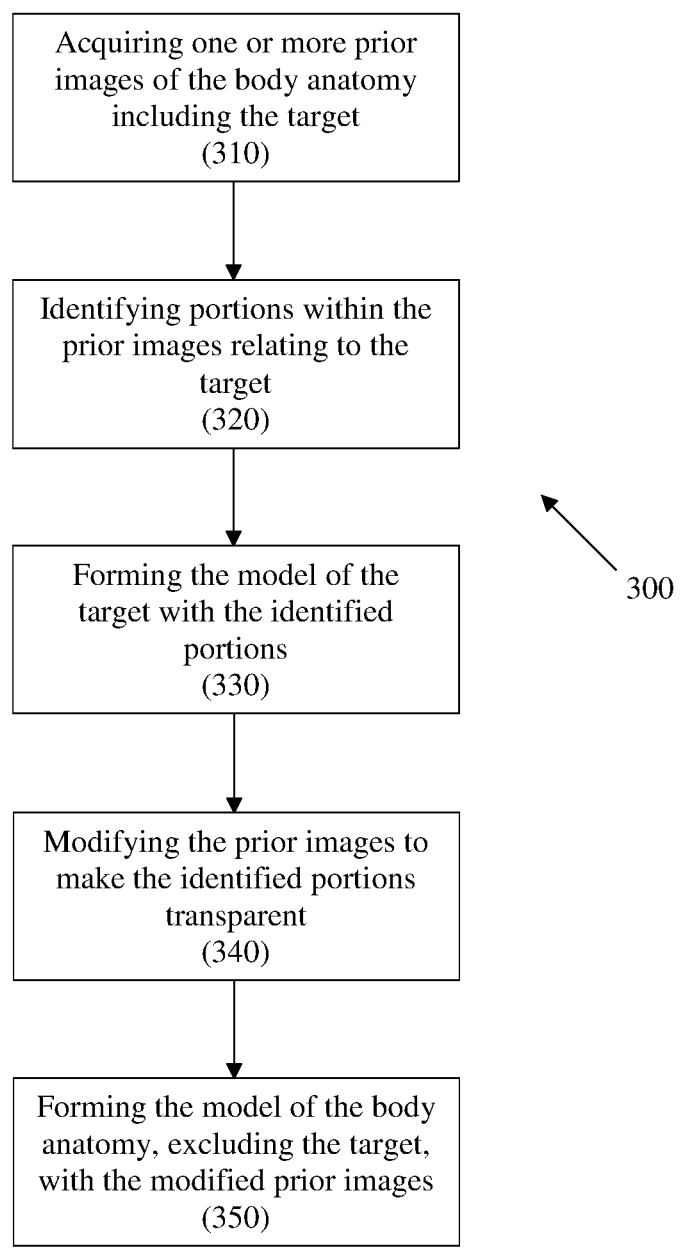
FIG. 3 illustrates an example method for providing a model of the target and a model of the body anatomy.

Referring to FIG. 3, there is illustrated an example method 300 for acquiring the model of the target and the model of the body anatomy. Method 300 includes step 310 of acquiring one or more prior images of the body anatomy including the target. Then, at step 320, identifying portions within the prior images relating to the target. Then, at step 330, forming the model of the target with the identified portions. Then, at step 340, modifying the prior images to make the identified portions transparent. Then, at step 350, forming the model of the body anatomy, excluding the target, with the modified prior images.

Referring to FIG. 2, there is illustrated an example embodiment of step 105, where a lung tumour (i.e. target) model 220 and a body anatomy model 230 of a patient are built from a pre-treatment 4D-CBCT image 210. This is done by separating, or extracting, the tumour image from the 4D-CBCT image. The resulting 4D tumour image is tumour model 220, while the 4D anatomic body image (without the tumour) is anatomic body model 210.

In one example, the process of separating the tumour image from the 4D-CBCT image is done by first warping a gross tumour volume (GTV) contour onto the 4D-CBCT image using deformable image restoration. The GTV contour may be acquired by contouring the tumour on a planning CT. For each phase of the 4D-CBCT, the image pixels within the warped contour are exported, or extracted, to form a tumour image. Similarly, for each phase of the 4D-CBCT, the values of the image pixels within the warped contour are set to zero attenuation, to form a "tumour-removed" body anatomy image. Multiple phases of the tumour images and the body anatomy images forms are used to generate 4D tumour images and 4D anatomic body images, and hence the tumour model and the body anatomy model, respectively.

The qualities of both models are highly dependent on the quality of the 4D-CBCT prior images. Different methodologies can be utilised to acquire the prior image. For example, a 4D-CBCT prior image may be constructed using the anatomical-adaptive image regularisation technique of Shieh et al (Shieh C C, Kipritidis J, O'Brien R T, Cooper B J, Kuncic Z and Keall P J 2015 Improving thoracic four-dimensional cone-beam CT reconstruction with anatomical-adaptive image regularization (AAIR) Phys. Med. Biol. 60(2), 841) to reduce noise and streaking artifacts while preserving image sharpness. A prior-image-constrained-compressed-sensing (PICCS) algorithm, such as that provided by Chen et al (Chen G H, Tang J and Leng S 2008 Prior image constrained compressed sensing (PICCS): A method to accurately reconstruct dynamic CT images from highly undersampled projection data sets Med. Phys. 35(2), 660-663), may further be used to improve the contrast of a bony anatomy.

In another example, sets of tomographic images of the patient that are typically acquired for patient setup immediately before radiotherapy treatment, are suitable prior images because they very closely represent the patient anatomy during the treatment.

More details on the steps of method 100 as illustrated in FIG. 2 are provided below.

Step 110

Figure 4:
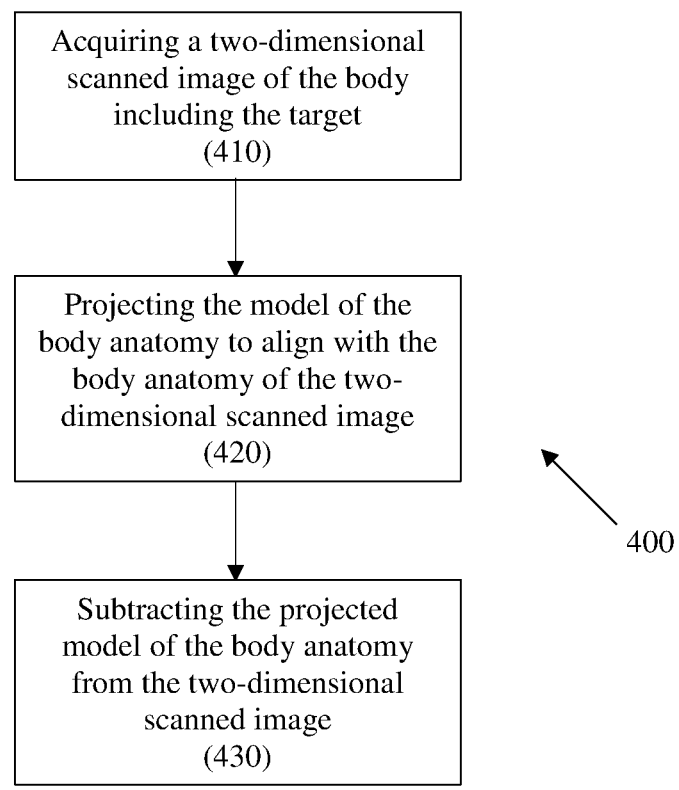
FIG. 4 illustrates an example method for acquiring a two-dimensional image of the target.

Referring to FIG. 4, there is illustrated an example method for processing a two-dimensional scanned image of the body including the target to obtain a two-dimensional image of the target. Method 400 includes step 410 of acquiring a two-dimensional scanned image of the body including the target. The two-dimensional scanned image of the body including the target preferably illustrates anatomical features of the body (i.e. body anatomy) in the vicinity of the target. Then, at step 420, projecting the model of the body anatomy to align with the body anatomy of the two-dimensional scanned image. Then, at step 430, subtracting the projected model of the body anatomy from the two-dimensional scanned image.

In some examples, the two-dimensional scanned image of the body including the target is acquired by a diagnostic medical imaging modality. In some examples, the scanning device is a diagnostic medical imaging device. In some examples, the two-dimensional scanned image further includes a surrogate signal. In some examples, the two-dimensional scanned image is an X-ray image projection. In more specific examples, the two-dimensional scanned image is a kV X-ray image projection.

A short imaging arc may be used to acquire the kV projection for a two-dimensional scanned image. In some examples, an arc size of nine degrees may be chosen. Experiments have found that nine degrees is the smallest arc size that renders successful tracking. Compared to using a single projection, a nine-degree arc exploits the 3D information of the tumour in multiple views, making it possible to track cases that would otherwise be challenging, e.g. tumours attached to neighbouring structures. In addition, a nine-degree imaging arc can be acquired in 1.5-9 seconds with a typical gantry speed of 1-6 deg/s, which is in general a sufficiently short time interval for the time resolution required for treatment guidance. A larger arc of thirty degrees was tested and found to slightly improve tumour localisation, but at the same time further degrade the time resolution, leading to overall similar tracking performance. In practice, the optimal arc size may depend on multiple factors such as the visibility, size, and location of the tumour, and gantry speed.

In some examples, method 400 is at least partially implemented, or run, through a graphics processing unit (GPU).

Referring to FIG. 2, there is illustrated an example embodiment of step 110, showing a two-dimensional scanned image which is a kV projection 240 of the body anatomy including the lung tumour (i.e. target). Also shown is a projection, or forward-projection, 250 of the model of the body anatomy to align with the body anatomy in kV projection 240.

For acquiring model projection 250, the respiratory phase in kV projection 240 is first determined, for example, by using the projection intensity analysis method of Kavanagh et al (Kavanagh A, Evans P M, Hansen V N and Webb S 2009 Obtaining breathing patterns from any sequential thoracic x-ray image set Phys. Med. Biol. 54(16), 4879). In other examples, the real-time phase can be calculated using the method proposed by Ruan et al (Ruan D, Fessler J A, Balter J M and Keall P J 2009 Real-time profiling of respiratory motion: baseline drift, frequency variation and fundamental pattern change Phys. Med. Biol. 54(15), 4777-4792). Preferably, the body anatomy model used has the same phase as the phase of kV projection 240. For example, where the body anatomy model is generated using 4D-CBCT, an image having the same phase as kV projection 240 may be selected for producing model projection 250. In the example embodiment of FIG. 2, this is done by forward projecting the tumour-removed 4D-CBCT image of the same phase as kV projection 240 to generate tumour-removed digitally reconstructed radiographs (DRRs) at the gantry angles used to acquire kV projection 240.

Finally, a two-dimensional, or projected, image 260 of the tumour is generated by subtracting model projection 250 (i.e. the DRR image) from kV projection 240. The difference projection thus acquired is assumed to contain only attenuation contributed from the tumour, therefore the tumour position can be measured by matching the tumour model with two-dimensional image 260. In practice however, exact subtraction of anatomies from the projections might not possible, or might be difficult, due to the change in body anatomy during treatment and due to approximation errors from the reconstructed 4D-CBCT images and DRRs.

Step 120

Prediction step 120 estimates the likely tumour position prior to measurement using a state transition model. The state transition model describes how the tumour position is likely to evolve from a previous frame (k−1) to a current frame k based on some prior knowledge of the nature of the motion to be tracked. The state transition model may be derived from the model of the target, from the model of the body anatomy, and/or from any other information that is available regarding the target and the body (e.g. information from a surrogate signal).

Where information on the motion of the target is available (e.g. through prior images and/or a surrogate signal) prediction step 120 may take this information into account to provide a more accurate estimate of the first present dataset of the target. Therefore, the motion information may be incorporated in the model of the target or in the state transition model.

In cases where the target is a lung tumour, in some examples the model of the target accounts for the periodic (or quasiperiodic) nature of lung tumour motion (e.g. due to respiration). In some examples, predicting the first present dataset of the target further comprises accounting for the periodic nature of lung tumour motion.

Referring to FIG. 2, there is illustrated an example embodiment of prediction step 120. For lung tumour motion, which is periodic or quasiperiodic due to respiration, the state transition model can be built using the 4D-CBCT prior image and the respiratory phases of the (k−1)'th and k'th frame. The model of the target and/or the model of the body anatomy may be used to calculate the displacements in tumour position from one phase bin l to another phase bin m, $d_l^m$. In some examples, the prior images, such as 4D-CBCT images, may be used to calculate $d_l^m$.

The predicted tumour position for the current frame, $\hat{x}_{k|k-1}$, may then be estimated to be the prior displacement vector between the previous and the current phase bin, $d_{PhaseBin_{k-1}}^{PhaseBin_k}$, added on top of the previously tracked tumour position, $\hat{x}_{k-1|k-1}$:

$$\hat{x}_{k|k-1} = \hat{x}_{k-1|k-1} + d_{PhaseBin_{k-1}}^{PhaseBin_k}. \quad (1)$$

The $d_{PhaseBin_{k-1}}^{PhaseBin_k}$ term incorporates the periodic nature of the respiratory motion into the prediction while the $\hat{x}_{k-1|k-1}$ term takes the baseline shifts into account. For the example illustrated in FIG. 2, the respiratory phase bin for each frame may be calculated retrospectively by the projection intensity analysis method. In one example the projection intensity analysis method is that of Kavanagh et al (Kavanagh A, Evans P M, Hansen V N and Webb S 2009 Obtaining breathing patterns from any sequential thoracic x-ray image set Phys. Med. Biol. 54(16), 4879).

Preferably, though not necessarily, the measure of the uncertainty of the first present dataset is a predicted covariance matrix of a distribution of the target's position. In some examples, the predicted covariance matrix is a function of an uncertainty of the state transition model (i.e. matrix $Q_k$ below). The uncertainty of the state transition model may be attributed to the respiratory-correlated prediction model. In some examples, the uncertainty of the state transition model is calculated using the target's positions tracked in a past time frame. In some examples, the past time frame spans from the present to ten seconds in the past. In other examples, other time frame lengths may be selected (e.g. 1, 2, 3, or more seconds).

The use of a limited time frame for calculating, or estimating, the uncertainty of the state transition model is different from past methods which made use of all previously tracked positions. A limited, or shorter, time frame is important for cases where the motion pattern changes constantly.

The predicted covariance matrix, $P_{k|k-1}$, is predicted from the previous covariance update, $P_{k-1|k-1}$, by:

$$P_{k|k-1} = F_{k-1} P_{k-1|k-1} F_{k-1}^T + Q_k \quad (2)$$

$Q_k$ is the prediction covariance matrix that describes the uncertainty of the state transition model, which can be estimated by the covariance matrix of the distribution of previously tracked tumour positions. In some examples, tracked tumour positions within the past ten seconds are empirically chosen to estimate $Q_k$. In other examples, prediction covariance matrix $Q_k$ may be estimated using any number of past tracked target positions. $F_{k-1}$ is the Jacobian of the right-hand side of Equation 1. Since the dr displacement vectors are calculated prior to treatment and are independent of tracking, $F_{k-1}$ reduces to the identity matrix I for all k. Equation 2 thus simplifies to:

$$P_{k|k-1} = P_{k-1|k-1} + Q_k. \quad (3)$$

To initialise Equations 1 and 3 for the first tracking frame, $\hat{x}_{0|0}$ may be set to the tumour position at any arbitrary phase of the 4D-CBCT. $Q_0$ may be set to equal the covariance matrix of the distribution of tumour positions observed from all phases of the 4D-CBCT.

In some examples, the state transition model predicts the target position to be the mean position within the same motion phase within the past 10-140 seconds, and the uncertainty of the state transition model is estimated to be the covariance matrix of the target positions within the same motion phase within the past 10-140 seconds. That is, in some examples, the present position value of the target in the first present dataset equals a mean position of the target within a same motion phase of the target in the past 10 seconds to 140 seconds, and wherein the uncertainty of the state transition model is estimated to equal a covariance matrix of the target's positions within the same motion phase in the past 10 seconds to 140 seconds.

Step 130

Measurement of the second present dataset is performed on the two-dimensional image of the target. Measurement is done by template-matching the two-dimensional image of the target with the model of the target. In some examples, the two-dimensional image is processed prior to template-matching. Preferably, though not necessarily, a template-matching metric is calculated, or estimated, in measurement step 130, either during or after template-matching has occurred. In some examples, the template matching metric is the Mattes Mutual Information (MMI) metric of Mattes et al (Mattes D, Haynor D, Vesselle H, Lewellen T and Eubank W 2001 Nonrigid multimodality image registration MEDICAL IMAGING: 2001: IMAGE PROCESSING, PTS 1-3 4322, 1609-1620. Medical Imaging 2001 Conference, SAN DIEGO, Calif., Feb. 18-22, 2001). In other examples, the template matching metric is the Normalized Cross Correlation (NCC) metric. In some examples, the measure of the uncertainty of the second present dataset is a function of the template-matching metric.

In some examples, step 130 involves taking some form of measurement, $z_k$, that can be related to the state variable by $z_k = h_k(x_k) + v_k$, where $h_k(\bullet)$ is the measurement response function and $v_k$ is the measurement noise. For kV-based tumour tracking, $z_k$ is the 2D tumour position measured on the kV detector plane, or on the imaging plane of the scanning device. $h_k(\bullet)$ is the 3D-to-2D forward-projection transformation that converts a 3D position in the patient coordinate space to its corresponding 2D position in the kV detector coordinate space for the current kV angle.

To measure $z_k$, the tumour model of the current phase bin is forward-projected and aligned with the anatomy-subtracted two-dimensional image by template matching. The template matching is performed using the Mattes Mutual Information (MMI) metric of Mattes et al (Mattes D, Haynor D, Vesselle H, Lewellen T and Eubank W 2001 Nonrigid multimodality image registration MEDICAL IMAGING: 2001: IMAGE PROCESSING, PTS 1-3 4322, 1609-1620. Medical Imaging 2001 Conference, SAN DIEGO, Calif., Feb. 18-22, 2001), with a higher MMI value indicating a better match. In some examples, a 20 mm by 20 mm search window centred at the forward-projected position of the predicted 3D tumour centroid is used. In other examples, other search window sizes may be used.

Preferably, the second present dataset further includes a measure of an uncertainty in the two-dimensional present position value of the target. In some examples, the measure of the uncertainty in the two-dimensional present position value of the target is a function of the template-matching metric.

The measure of the uncertainty of the measurement process, i.e. 2D template matching, is described by the 2-by-2 measurement covariance matrix, $R_k$. In this work, $R_k$ is estimated to be a diagonal matrix, because the template matching errors in the kV-lateral and kV-vertical directions are generally independent of each other. For MMI values higher than a fixed threshold, both diagonal entries are set to the square of the kV projection pixel size. For MMI values lower than a given threshold, both diagonal entries are set to be the square of the size of the search window (e.g. 20 mm). In some examples, the value of the MMI threshold is empirically set to be 0.4. In other examples, the MMI threshold may be set to any other value, such as 0.1, 0.2, or 0.3.

The fact that the measure of the uncertainty of the measurement process takes into account, or incorporates, the template-matching metric (e.g. the MMI value) is advantageous for markerless tumour tracking because template-matching in markerless tracking suffers from significantly larger uncertainty than marker tracking due to the inferior visibility of the tumour on 2D images (e.g. kV projections).

In some examples, template-matching is implemented, or run, through a GPU.

Steps 140 and 150

Step 140 combines the prediction and the measurement of steps 120 and 130, respectively, to estimate both x and P according to the following equations:

$$\hat{x}_{k|k} = \hat{x}_{k|k-1} + K_k[z_k - h_k(i_{k|k-1})], \quad (4)$$

$$\hat{P}_{k|k} = (I - K_k H_k) P_{k|k-1}. \quad (5)$$

At step 150, equations 4 and 5 further update the values of the previous dataset whereby a next iteration (k+1) of method 100 will rely on $\hat{x}_{k|k}$ and $\hat{P}_{k|k}$ as the previous dataset in prediction step 130.

The $[z_k - h_k(\hat{x}_{k|k-1})]$ term in Equation 4 represents the discrepancy between the prediction and the measurement. The Kalman gain, $K_k$, describes how much each component of the prediction state needs to be corrected towards the measurement, and is calculated by:

$$K_k = P_{k|k-1} H_k^T (H_k P_{k|k-1} H_k^T + R_k)^{-1}, \quad (6)$$

where $H_k$ is the Jacobian of $h_k(\cdot)$. It can be seen from Equation 6 that the Kalman gain takes into account the angular-dependent 3D-to-2D geometry via $H_k$, the distribution of tumour 3D positions via $P_{k|k-1}$, and the reliability of the template matching result via $R_k$. The inclusion of $P_{k|k-1}$ exploits the correlations between motion components in different directions, making 3D tracking possible even though the measurement vector $z_k$ contains only information on the kV detector plane (i.e. 2D information of tumour position projected on the kV detector plane).

The implementation of a Bayesian framework (or an extended Kalman filter based on the same) for markerless tumour tracking is advantageous for several reasons. Firstly, conventional template-matching-based tracking methods are rarely able to continuously track the tumour due to inferior tumour visibility. By combining motion prediction and measurement uncertainty estimation with template matching, method 100 is able to track the tumour even when a good template match is not possible. Secondly, the use of the covariance matrix of tumour position distribution is advantageous for estimating the motion component along the measurement beam (e.g. X-ray or kV beam) direction, i.e. the direction of the beam scanning device used to acquire the two-dimensional image of the body including the target, enabling 3D tumour tracking using only 2D imaging. Although the example of FIG. 2 illustrates an example implementation of method 100 for the purpose of tumour tracking, method 100 and the above framework may be used for any 3D target localisation application that relies on 2D imaging.

In some examples, provisions may be taken to speed up the execution of method 100. In some examples, the real-time respiratory phase calculation method proposed by Ruan et al (Ruan D, Fessler J A, Balter J M and Keall P J 2009 Real-time profiling of respiratory motion: baseline drift, frequency variation and fundamental pattern change *Phys. Med. Biol.* 54(15), 4777-4792) may be used in prediction step 120 to replace retrospective phase calculation. In some examples, the processing of the two-dimensional image of the body including the target in step 110 (e.g. through method 400) and template-matching in step 130 may contribute to about 95% of the computation time of method 100. Both of these steps are highly parallelisable and can be significantly sped up through GPU implementation.

In some examples, step 110 of processing the two-dimensional scanned image of the body including the target and step 130 of measuring a second present dataset of the target by template matching are executed in parallel. In some examples, step 110 of processing the two-dimensional scanned image of the body including the target and/or step 130 of measuring a second present dataset of the target by template matching are at least partially implemented through a GPU. In some cases, GPU implementation of steps 110 and 130 provides a computation time of less than 1 second, which is advantageous for real-time applications. In some examples, step 120 is executed in parallel to step 110. In some examples, step 120 is executed in parallel to step 130.

In some examples, method 100 is implemented using the Insight Toolkit (ITK) of Johnson et al (Johnson H J, McCormick M, Ibañez L and Consortium T I S 2015 *The ITK Software Guide* Kitware, Inc. ISBN 1-930934-27-0) and/or the Reconstruction Toolkit (RTK) of Rit et al (Rit S, Oliva M V, Brousmiche S, Labarbe R, Sarrut D and Sharp G C 2014 The Reconstruction Toolkit (RTK), an open-source cone-beam CT reconstruction toolkit based on the Insight Toolkit (ITK) *J. Phys.: Conf. Ser.* 489(1), 012079-012079).

In some examples, there is provided a method for three-dimensional tracking of a target within a body. The method includes the step of acquiring, by a scanning device, a two-dimensional image of the body including the target. The method further includes the step of processing, by a processing system and/or a graphics processing unit, the two-dimensional image of the body including the target to obtain a two-dimensional image of the target (i.e. a two-dimensional image illustrating only the target). The method further includes the step of predicting, by the processing system, a first present dataset of the target by using a previous dataset of the target and a state transition model, wherein the first present dataset includes at least a three-dimensional present position value of the target, and wherein the previous dataset includes at least a three-dimensional previous position value of the target. The method further includes the step of measuring a second present dataset of the target by template-matching, by the processing system and/or the graphics processing unit, of the two-dimensional image of the target with a model of the target, wherein the second present dataset includes at least a two-dimensional present position value of the target. The method further includes the step of estimating, by the processing system, a third present dataset of the target by statistical inference using the first present dataset and the second present dataset, wherein the third present dataset includes at least a three-dimensional present position value of the target. The method further includes the step of updating, by the processing system, the previous dataset of the target to match the third present dataset.

Figure 5:
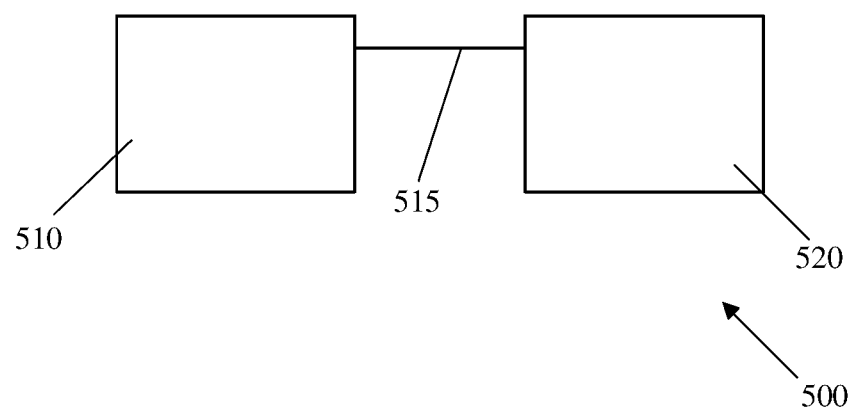
FIG. 5 illustrates an example system for three-dimensional tracking of a target located within a body.

Referring to FIG. 5, there is illustrated an example system 500 for three-dimensional tracking of a target located within a body, including a scanning device 510 configured to acquire a two-dimensional scanned image of the body including the target. System 500 further includes a processing system 520. Processing system 520 is configured to receive and process the two-dimensional scanned image of the body including the target to obtain a two-dimensional image of the target. Processing system 520 is further configured to predict a first present dataset of the target by using a previous dataset of the target and a state transition model. The first present dataset includes at least a three-dimensional present position value of the target. The previous dataset includes at least a three-dimensional previous position value of the target. Processing system 520 is further configured to measure a second present dataset of the target by template-matching of the two-dimensional image of the target with a model of the target. The second present dataset includes at least a two-dimensional present position value of the target. Processing system 520 further estimates a third present dataset of the target by statistical inference using the first present dataset and the second present dataset. The third present dataset includes at least a three-dimensional present position value of the target. Processing system 520 further updates the previous dataset of the target to match the third present dataset.

Scanning device 510 may be an X-ray imaging device, or a kV imaging device, including an X-ray source and an X-ray detector. In some examples, scanning device 510 is a CT scanner or a diagnostic imaging device. In some examples, scanning device 510 is any device able to acquire a two-dimensional, or projected, image of the target located within the body. Scanning device 510 may further include a detector for detecting a surrogate signal. In some examples, scanning device 510 may include one or more (e.g. two, three, four or more) of any of the above-mentioned scanning devices. The scanned image of the body including the target may be an X-ray image, a kV image, a CT scan or any other type of image or set of images illustrating the target within the body, in accordance with scanning device 510.

Scanning device 510 may be in communication with processing system 520. Communication between scanning device 510 and processing system 520 may occur either through a wired or wireless connection. Each of scanning device 510 and processing system 520 may include further apparatus necessary for communication (e.g. transmitter and receiver). Preferably, though not necessarily, system 500 further includes a communication link 515 between scanning device 510 and processing system 520. Communication link 515 may be wired or wireless. Processing system 520 may be located within scanning device 510, or in proximity of scanning device 510, or remotely of scanning device 510. Communication link 515 allows transmission of the scanned image from scanning device 510 to processing system 520. Communication link 515 may further allow for transmission of any other data between scanning device 510 and processing system 520 (e.g. data from a surrogate signal).

In some examples, the two-dimensional scanned image of the body including the target illustrates anatomy of the body in the vicinity of the target. In those examples, in order to obtain the two-dimensional image of the target (excluding the body anatomy), processing system 520 may process the two-dimensional scanned image to remove the images of the body anatomy and isolate the image of the target. To this end, processing system 520 may project a model of the body anatomy excluding the target to align with the body anatomy of the two-dimensional scanned image and subtract the projected model of the body anatomy from the two-dimensional scanned image.

In some examples, processing system 520 further includes a graphics processing unit (GPU) or a visual processing unit (VPU). The GPU may be used to accelerate the measurement of the second present dataset by accelerating the template-matching process. In some examples, processing system 520 comprises a memory unit. The memory unit may store the model of the target and/or the model of the body anatomy excluding the target.

Figure 6:
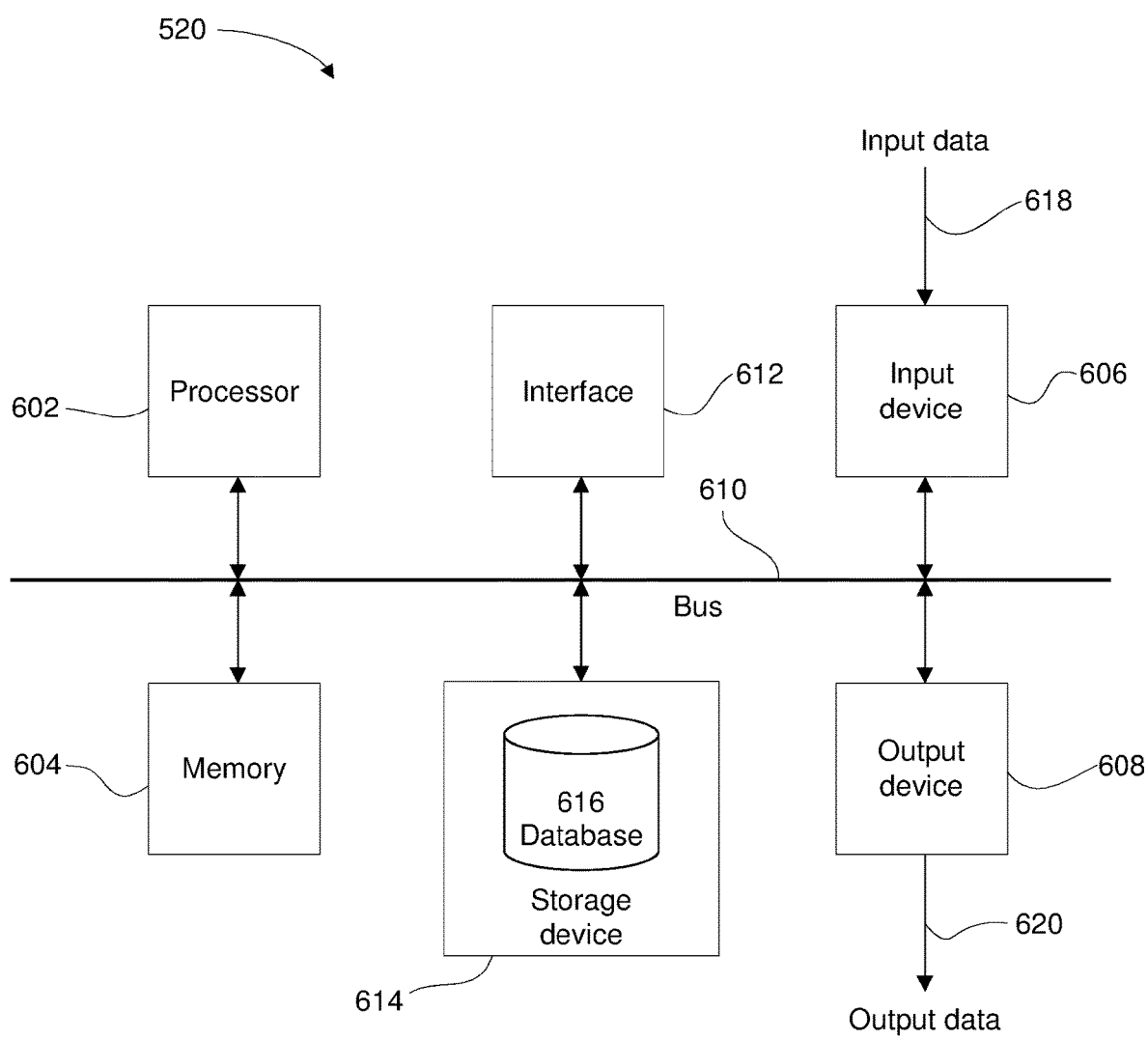
FIG. 6 illustrates an example processing system for use in the system of FIG. 5.

Referring to FIG. 6, there is illustrated an example processing system 520. In particular, the processing system 520 generally includes at least one processor 602, or processing unit or plurality of processors, memory 604, at least one input device 606 and at least one output device 608, coupled together via a bus or group of buses 610. In certain embodiments, input device 606 and output device 608 could be the same device. An interface 612 can also be provided for coupling the processing system 520 to one or more peripheral devices, for example interface 612 could be a PCI card or PC card. At least one storage device 614 which houses at least one database 616 can also be provided. The memory 604 can be any form of memory device, for example, volatile or non-volatile memory, solid state storage devices, magnetic devices, etc. The processor 602 could include more than one distinct processing device, for example to handle different functions within the processing system 600.

Input device 606 receives input data 618 and can include, for example, a data receiver or antenna such as a modem or wireless data adaptor, data acquisition card, etc. Input data 618 could come from different sources, for example scanning device 510 and/or with data received via a network. Output device 608 produces or generates output data 620, for example representing position values, two-dimensional images and/or three-dimensional images, and can include, for example, a display device or monitor in which case output data 620 is visual, a printer in which case output data 620 is printed, a port for example a USB port, a peripheral component adaptor, a data transmitter or antenna such as a modem or wireless network adaptor, etc. Output data 620 could be distinct and derived from different output devices, for example a visual display on a monitor in conjunction with data transmitted to a network. A user could view data output, or an interpretation of the data output, on, for example, a monitor or using a printer. The storage device 614 can be any form of data or information storage means, for example, volatile or non-volatile memory, solid state storage devices, magnetic devices, etc.

In use, the processing system 520 is adapted to allow data or information to be stored in and/or retrieved from, via wired or wireless communication means, the at least one database 616. The interface 612 may allow wired and/or wireless communication between the processing unit 602 and peripheral components that may serve a specialised purpose. The processor 602 receives instructions as input data 618 via input device 606 and can display processed results or other output to a user by utilising output device 608. More than one input device 606 and/or output device 608 can be provided. It should be appreciated that the processing system 520 may be any form of terminal, server, specialised hardware, or the like.

In some examples, system 500 is configured to implement method 100.

Figure 7:
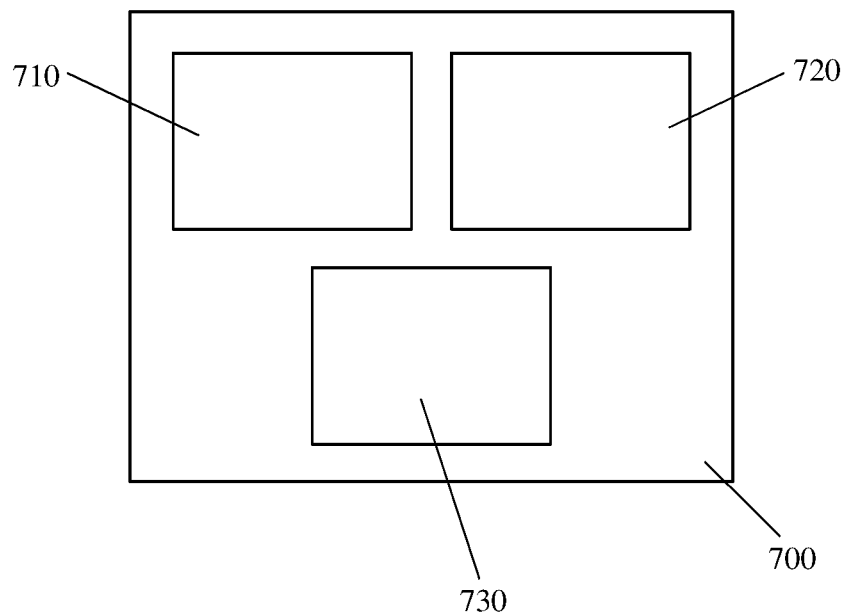
FIG. 7 illustrates an example system for tracking and interacting with a target located within a body.

System 500 may further include an apparatus for interacting with, or operating on, the target. Referring to FIG. 7, there is illustrated a system 700 for tracking and interacting with a target located within a body. System 700 includes a scanning device 710, a processing system 720, and an apparatus 730. Scanning device 710 acquires a two-dimensional scanned image of the body including the target. Processing system 720 receives the two-dimensional scanned image and executes, or implements, method 100, outputting a third present dataset that includes at least a three-dimensional present position value of the target. Apparatus 730 interacts with, or operates on the target and is adjusted, or its operation is adjusted, in response to, or based on, the third present dataset. In some examples, system 700 may further include one or more controllers for adjusting the operation of apparatus 730.

In some examples, where the target is a tumour or lung tumour, system 700 is a radiotherapy system. In some examples, apparatus 730 is a treatment apparatus. In some examples, apparatus 730 is a therapeutic radiation source. In some examples, the direction of radiation output is adjusted in response to, or based on, the third present dataset. In some examples, apparatus 730 is a patient table. In some examples, the position and/or orientation of the table is adjusted in response to, or based on, the third present dataset. In other examples, apparatus 730 is any type of device that is part of a radiotherapy system and whose operation would need to be adjusted in response to tumour motion.

Figure 8:
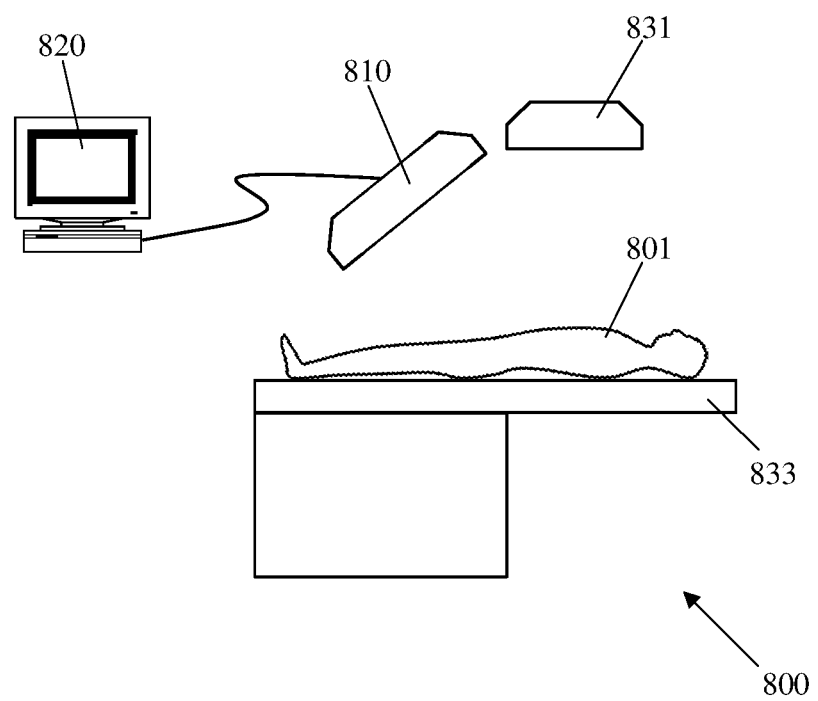
FIG. 8 illustrates an example radiotherapy system for tracking and treating a tumour located within a body.

With reference to FIG. 8, there is illustrated an example radiotherapy system 800 for tracking and treating a tumour located within a body (e.g. patient 801). Radiotherapy system 800 includes a scanning device 810, a processing system 820, a therapeutic radiation source 831, and a patient table or couch 833. Any one or more of scanning device 810, processing system 820, radiation source 831, and patient table 833 may be integrated, or in-built, into a radiotherapy system (i.e. a radiotherapy machine), or they may be provided as separate elements in radiotherapy system 800.

During treatment, scanning device 810 continuously, or repeatedly, acquires two-dimensional kV X-ray scanned images of the patient and sends each scanned image (or a processed version of said scanned image) to processing system 820. Processing system 820 executes method 100 for each scanned image received, and estimates a third present dataset, which includes a three-dimensional position of the tumour.

In some examples, processing system 820 is configured to adjust radiation source 831 and/or patient table 833 in response to the tumour's motion indicated by the third present dataset. In other examples, the estimated third present dataset is sent, transmitted, or transferred to another processing system (not shown) or to a human operator who may then determine how to adjust radiation source 831 and/or patient table 833.

In some examples, adjustment of radiation source 831 may include adjustment of the direction of radiation output to redirect a treatment beam to follow the tumour motion. In some examples, adjustment of radiation source 831 may further include pausing, stopping, or reducing radiation output if the tracked three-dimensional position of the tumour exceeds a certain prescribed range, and resuming the treatment beam when the three-dimensional position of the tumour returns within the prescribed range. In some examples, adjusting patient table 833 includes adjusting a position and/or orientation of patient table 833 to maintain the tumour position in a path of therapeutic radiation from radiation source 831.

Adjustment of radiation source 831 and/or patient table 833 may be done by controllers (not shown). In some examples the controllers are electrical controllers. In some examples, the controllers are mechanical controllers. The controllers may be electrically or mechanically controlled by processing system 820, or by any other processing system, or by a human operator in response to the third present dataset estimated through method 100 or by system 800.

Adjustment of a treatment apparatus (e.g. a therapeutic radiation source and/or a patient table) in response to tumour motion tracked by method 100 or by system 700 is advantageous since it enables continuous, uninterrupted treatment. In some cases, adjustment of treatment apparatus further enables tailoring of treatment to suit the conditions of a moving tumour, and it may further minimise radiation damage to tissue surrounding the tumour. These advantages provide an improved treatment method and/or system due to reduce treatment time and recovery time.

FURTHER EXAMPLES

The following examples provide more detailed discussion of particular embodiments. The examples are intended to be merely illustrative and not limiting to the scope of the present invention.

Example 1: Patient Data

The proposed method was retrospectively validated on a total of 13 clinical cases from two different sets of patient data:
(i) The CBCT cases (11 cases): CBCT projections from an NCI-sponsored trial with locally advanced lung cancer patients. This dataset was included and described in a previous publication (Shieh C C, Keall P J, Kuncic Z, Huang C Y and Feain I 2015 Markerless tumor tracking using short kilovoltage imaging arcs for lung image-guided radiotherapy Phys. Med. Biol. 60(24), 9437). More details on the datasets can be found in Roman et al (Roman N O, Shepherd W, Mukhopadhyay N, Hugo G D and Weiss E 2012 Interfractional positional variability of fiducial markers and primary tumors in locally advanced non-small-cell lung cancer during audiovisual biofeedback radiotherapy Int. J. Radiat. Oncol. 83(5), 1566-1572).
(ii) The SABR cases (2 cases): kV images during MV beam-on from a lung SABR trial (NCT02514512).

The CBCT cases included 11 CBCT scan pairs from four locally advanced lung cancer patients with central tumours, which often suffer from inferior adjacent contrast on kV images due to being attached to the mediastinum and are challenging to track. The sizes of the tumours ranged from 30.2 $cm^3$ to 88.9 $cm^3$. Each patient was implanted with 2-4 fiducial markers around the tumour, the trajectories of which were used as ground truths to quantify the errors of markerless tumour tracking implemented through method 100.

Each CBCT scan pair contained two CBCT scans that were acquired within the same day. The first scan in the pair was used as the pre-treatment CBCT to build the tumour and body anatomy models, while markerless tumour tracking was performed on the second scan. The tumour positions between some of the scan pairs were misaligned as the time gap between the two scans ranged from a half to a couple of hours.

To simulate pre-treatment patient alignment, the pre-treatment CBCT as well as the tumour and body anatomy models were rigidly shifted to align with the mean tumour position within the first 10 seconds of the second scan. Markers were removed from the projection images to avoid biasing the markerless tracking results. Each CBCT scan contained either 1200 or 2400 half-fan projections acquired with a frame rate of about 5 Hz from the Varian on-board kV imaging device (Varian Medical Systems, Palo Alto, Calif.). The size of each projection was 1024 pixels by 768 pixels, with a pixel spacing of 0.388 mm. The pre-treatment 4D-CBCT (10 bins) was reconstructed using the anatomical-adaptive image regularisation (AAIR) technique (Shieh C C, Kipritidis J, O'Brien R T, Cooper B J, Kuncic Z and Keall P J 2015 Improving thoracic four-dimensional cone-beam CT reconstruction with anatomical-adaptive image regularization (AAIR) *Phys. Med. Biol.* 60(2), 841) combined with the prior-image-constrained-compressed-sensing (PICCS) algorithm (Chen G H, Tang J and Leng S 2008 Prior image constrained compressed sensing (PICCS): A method to accurately reconstruct dynamic CT images from highly undersampled projection data sets *Med. Phys.* 35(2), 660-663). Audiovisual biofeedback breathing guidance was performed during both CT and CBCT acquisitions.

Two patients (one fraction each) from a lung SABR trial (NCT02514512) designed to investigate the benefits of real-time adaptive treatment and kV imaging were included. The SABR cases represent realistic clinical scenarios for validating markerless tumour tracking for two main reasons. Firstly, the in-treatment kV images for tracking were acquired with the presence of MV scatter noise. Secondly, the pre-treatment CBCT scan was acquired with a standard protocol of one-minute scan time and around 680 half-fan projections. The first patient had a 7.4 cm³ tumour attached to the chest wall, while the second patient had a 13 cm³ tumour near the diaphragm. Each patient was implanted with three electromagnetic transponder beacons, the motions of which were sent to the multileaf-collimator to enable real-time treatment beam adaptation. The trajectories of the beacons were used as the ground truths to quantify the errors of markerless tumour tracking. The patients were treated on a Varian Triology (Varian Medial Systems, Palo Alto, Calif.). A one-minute pre-treatment CBCT scan was acquired for each fraction, and was reconstructed into a 10-bin 4D-CBCT using the PICCS algorithm (see, for example, Chen G H, Tang J and Leng S 2008 Prior image constrained compressed sensing (PICCS): A method to accurately reconstruct dynamic CT images from highly undersampled projection data sets *Med. Phys.* 35(2), 660-663) for building the tumour and anatomic models. Prior to treatment the patient was shifted such that the tumour was around the isocenter. The same shift was applied to the tumour and anatomic models. kV images were continuously acquired during treatment with a frame rate of about 5 Hz and pixel spacing of 0.388 mm. The field of view of the kV images was cropped to approximately 20 cm by 20 cm to reduce imaging dose. Beacons were removed from the kV images to avoid biasing the markerless tracking results. Audiovisual biofeedback breathing guidance was performed during CT, CBCT, and treatment.

Example 1: Electrochemical Measurements

The ground truth for evaluating tracking error was built from the trajectory of the fiducial marker (CBCT cases) or the electromagnetic beacon (SABR cases) that was closest to the tumour centroid. The trajectories of the fiducial markers were obtained using a robust template-based segmentation method (Poulsen P R, Fledelius W, Keall P J, Weiss E, Lu J, Brackbill E and Hugo G D 2011 A method for robust segmentation of arbitrarily shaped radiopaque structures in cone-beam CT projections *Med. Phys.* 38(4), 2151-2156) and a probability-density-function based on 2D-to-3D conversion (Poulsen P R, Cho B and Keall P J 2008 A method to estimate mean position, motion magnitude, motion correlation, and trajectory of a tumor from cone-beam CT projections for image-guided radiotherapy *Int. J. Radiat. Oncol.* 72(5), 1587-1596). The trajectories of the electromagnetic beacons were recorded by the Calypso Tracking System (Varian Medical Systems, Palo Alto, Calif.).

To relate marker/beacon positions to tumour position, a reference-to-tumour vector is calculated for each respiratory phase bin of the pre-treatment 4D-CBCT as the displacement from the mean marker/beacon centroid to the tumour centroid. The ground truth position at imaging frame k, $g_k$, is then the trajectory of the marker/beacon centroid plus the reference-to-tumour vector of the corresponding phase bin at frame k.

The tracking error at frame k, $e_k$, was defined by:

$$e_k^{Tracking} = \hat{x}_{k|k} - g_k, \quad (7)$$

where $\hat{x}_{k|k}$ is the 3D tumour position as estimated by the proposed markerless tumour tracking method 100. For each tracking fraction, the means and standard deviations of the left-right (LR), superior-inferior (SI), and anterior-posterior (AP) components of $e_k^{Tracking}$'s were calculated. The mean and standard deviation of the 3D error, $\|e_k^{Tracking}\|$, was also calculated.

To compare markerless tumour tracking with the current standard of care, i.e. a single estimation of tumour position based on the pre-treatment 3D CBCT, the standard-of-care error was defined by:

$$e_k^{Standard} = x_{3DCBCT} - g_k, \quad (8)$$

where $x_{3DCBCT}$ is the tumour position estimated from the pre-treatment 3D CBCT. Similarly to $e_k^{Tracking}$, the mean and standard deviation of $e_k^{Standard}$'s in each direction as well as its 3D norm were calculated for every fraction.

Example 1: Results

For imaging frames where the tumour can be visually identified, visual inspection suggested that the proposed markerless tumour tracking method was able to continuously track the tumours at every imaging angle for all 13 cases investigated. The mean and standard deviation of the 3D tracking error ranged from 1.55-2.88 mm and 0.63-1.46 mm, respectively. The 95th percentile of the 3D tracking error ranged from 2.62-5.77 mm. The 5th-to-95th percentile motion range observed from the ground truths was 1.38-5.51 mm for LR, 4.40-15.26 mm for SI, and 1.99-7.91 mm for AP.

Figure 9:
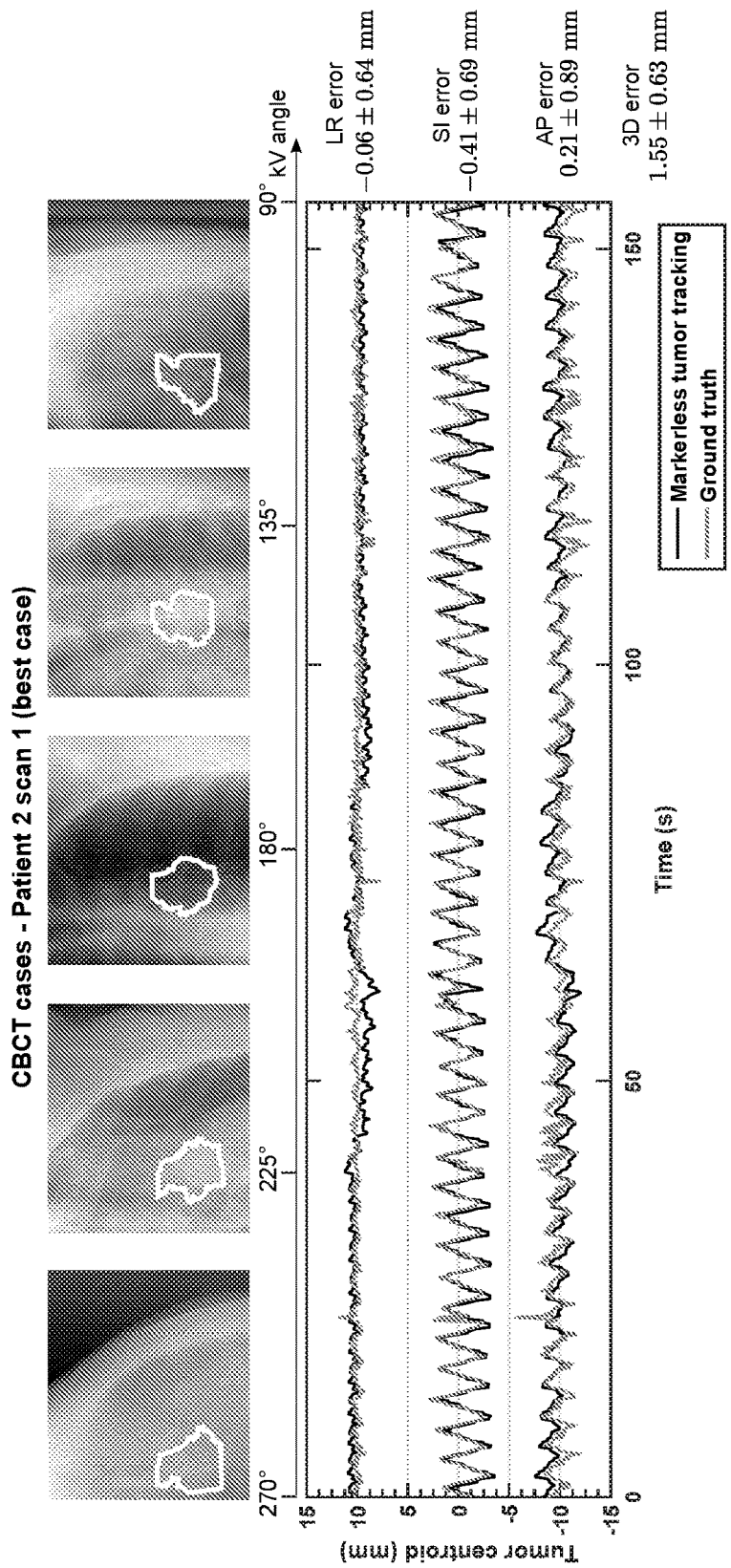
FIG. 9 illustrates example tumour trajectories tracked using the method of FIG. 1. Also illustrated are the example tumour trajectories tracked using a conventional marker-based method, for comparison.
Figure 10:
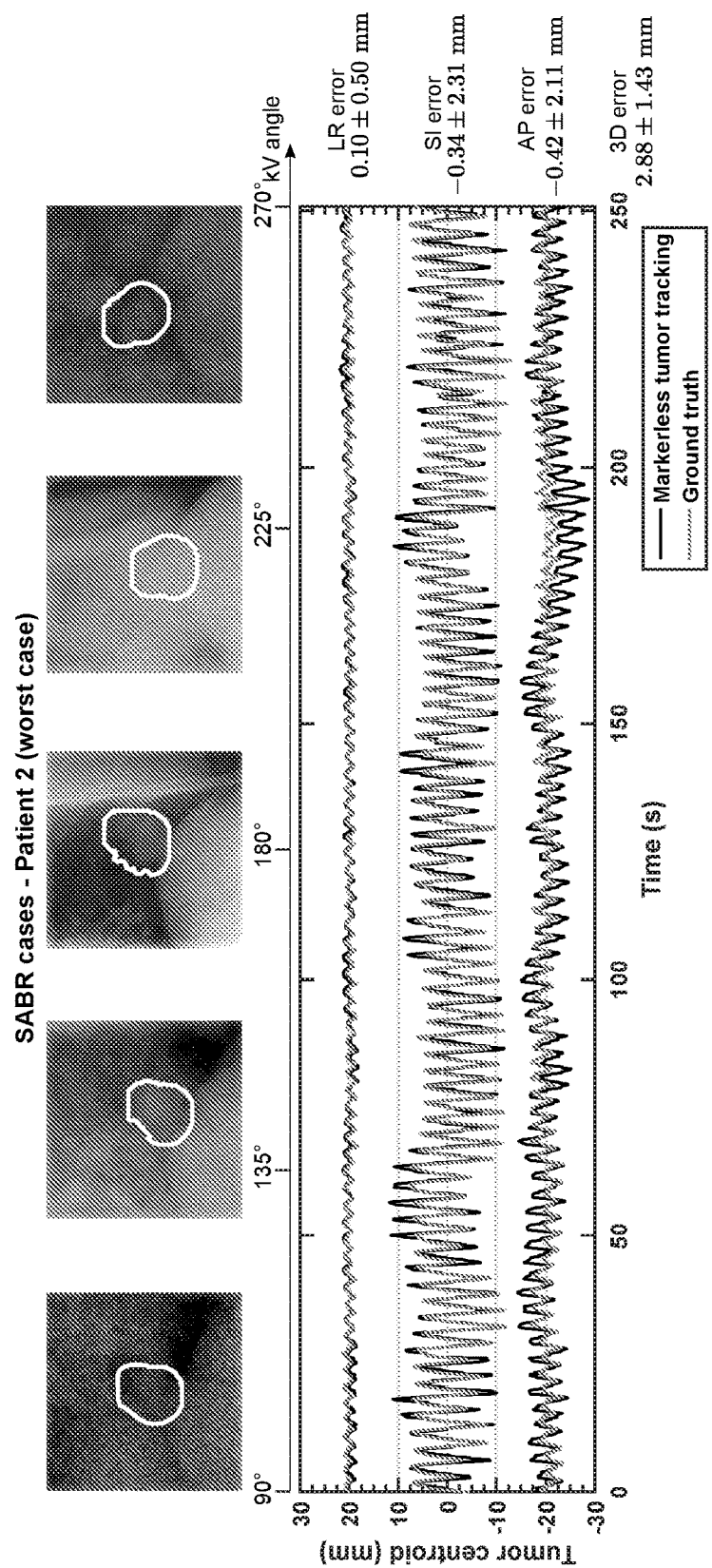
FIG. 10 illustrates further example tumour trajectories tracked using the method of FIG. 1. Also illustrated are the example tumour trajectories tracked using a conventional marker-based method, for comparison.

FIG. 9 illustrates the markerless tumour tracking trajectories of cases with the lowest 3D tracking error, where the mean values of the LR, SI, and AP trajectories were shifted for display to 10 mm, 0 mm, and −10 mm. FIG. 10 illustrates the markerless tumour tracking trajectories of cases with the highest 3D tracking errors, where the mean values of the LR, SI, and AP trajectories were shifted for display to 20 mm, 0 mm, and −20 mm.

The lowest mean 3D tracking error was found for the first scan pair of patient 2 of the CBCT cases, with a mean 3D error of 1.55±0.63 mm (shown in FIG. 9). Overall the tracking trajectory agreed closely with the ground truth, except for around t=60 s, where LR errors of about 3 mm were observed. The highest mean 3D tracking error was found for patient 2 of the SABR cases, with a mean 3D error of 2.88±1.43 mm (shown in FIG. 10). The larger tracking errors are likely attributed to the presence of MV scatter in the kV images and the lower quality of the tumour and anatomic models due to the limited amount of pre-treatment CBCT projections. The tumour motion range was also considerably larger for this case. Nevertheless, even in this challenging case the pattern of the motion was consistently tracked at every imaging angle.

Figure 11:
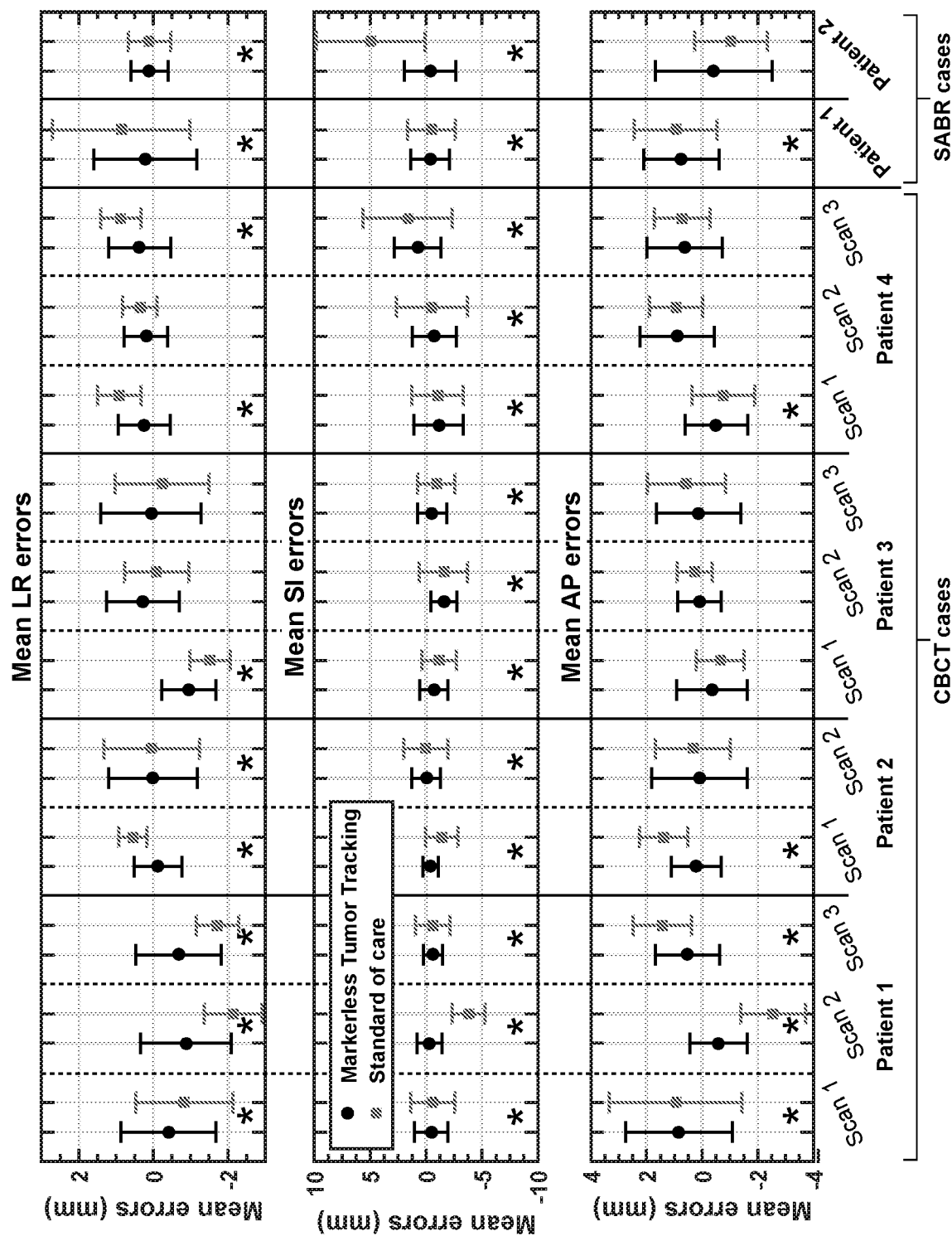
FIG. 11 illustrates mean tracking errors in the left-right (LR), superior-inferior (SI), and anterior-posterior (AP) directions for 13 example cases investigated using the method of FIG. 1.

FIG. 11 illustrates a comparison of the mean tracking errors in LR, SI, and AP to the standard-of-care errors for all 13 cases investigated. The standard deviations of the errors were plotted as error bars. Cases marked with asterisks indicate that the proposed markerless tumour tracking method resulted in significantly smaller errors than the standard of care.

The mean tracking errors were always closer to 0 mm than the mean standard-of-care errors in every direction, indicating the ability of the proposed method to track baseline shifts. The proposed markerless tumour tracking approach was found to perform the best in the SI direction. Tracking errors were significantly smaller than the standard-of-care errors for all cases in the SI direction (p-value less than 0.02 for patient 4 scan 1 of the CBCT cases and p-value less than $10^{-4}$ for all other cases), while only for 10 and 6 cases in the LR and AP directions, respectively (p-value less than 10).

Figure 12:
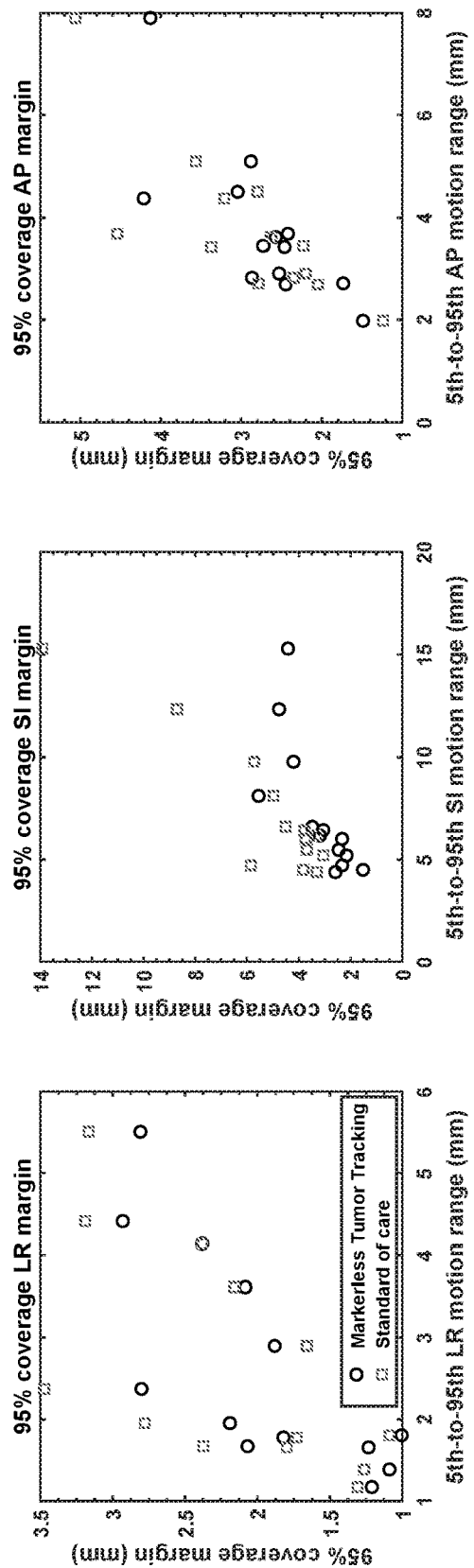
FIG. 12 illustrates a comparison between the markerless tumour tracking method and the standard of care in terms of the margins required to encompass 95% of tumour motion plotted with respect to the 5th-to-95th motion ranges in the LR, AP, and SI directions, for the 13 example cases investigated using the method of FIG. 1.

To investigate the benefits to patients of markerless tumour tracking over the standard of care, FIG. 12 compares the margins required with or without tracking to cover 95% of tumour motion in the LR, SI, and AP directions. Markerless tumour tracking always resulted in smaller margins in the SI directions with one exception.

Considerable reduction in SI margin was found for cases with greater than 10 mm 5th-to-95th SI motion range. For patient 2 of the SABR cases, the reduction in SI margin was as large as 9.5 mm (from 13.9 mm to 4.4 mm). Margin reduction in the LR and AP directions was less pronounced. Generally with markerless tumour tracking, a margin of 3 mm, 6 mm, and 4.5 mm in the LR, SI, and AP directions were sufficient to encompass 95% of tumour motion for all 13 cases investigated.

Results on the SABR cases demonstrated the ability of the proposed approach to handle practical challenges such as MV scatter and low CBCT image quality, and thus its practical feasibility. The benefits to patients of markerless tumour tracking over the standard of care was highlighted for patients with greater than 10 mm 5th-to-95th SI motion ranges, with up to 9.5 mm reduction in SI margin. The clinical implementation of the proposed method enables more accurate and precise lung radiotherapy using existing hardware and workflow.

There are however a number of limitations in the example implementation of method 100. A first limitation is that, while fiducial marker or beacon motions were used as the ground truths, these can have differential motions with the tumour. Hardcastle et al (Hardcastle N, Booth J, Caillet V, O'Brien R, Haddad C, Crasta C, Szymura K and Keall P 2016 Electromagnetic beacon insertion in lung cancer patients and resultant surrogacy errors for dynamic MLC tumour tracking *The 58th Annual Meeting of the American Association of Physicists in Medicine*, Washington D.C.) has reported 0-3 mm deviations between beacon and tumour motion. Another limitation is the inferior quality of the tumour and anatomic models for the SABR cases due to the challenge in reconstructing 4D-CBCT images using a one-minute scan. In practice, other improved algorithms for iterative 4D-CBCT reconstruction (see, for example, Schmidt M L, Poulsen P R, Toftegaard J, Hoffmann L, Hansen D and Srensen T S 2014 Clinical use of iterative 4D-cone beam computed tomography reconstructions to investigate respiratory tumor motion in lung cancer patients Acta Oncol. 53(8), 1107-1113. PMID: 24957556. URL: http://dx.doi.org/10.3109/0284186X.2014.927585) will likely further improve the performance of the proposed method for cases with one-minute pre-treatment CBCT scans as the prior images.

Optional embodiments may also be said to broadly include the parts, elements, steps and/or features referred to or indicated herein, individually or in any combination of two or more of the parts, elements, steps and/or features, and wherein specific integers are mentioned which have known equivalents in the art to which the invention relates, such known equivalents are deemed to be incorporated herein as if individually set forth.

Although a preferred embodiment has been described in detail, it should be understood that many modifications, changes, substitutions or alterations will be apparent to those skilled in the art without departing from the scope of the present invention.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The invention claimed is:

1. A method for three-dimensional tracking of a target located within a body, the method performed by at least one processing system, and comprising the steps of:
   processing a two-dimensional scanned image of the body including the target to obtain a two-dimensional image of the target, wherein the two-dimensional scanned image is acquired from a scanning device;
   predicting a first present dataset of the target by using a previous dataset of the target and a state transition model, wherein the first present dataset includes at least a three-dimensional present position value of the target, and wherein the previous dataset includes at least a three-dimensional previous position value of the target;
   measuring a second present dataset of the target by template-matching of the two-dimensional image of the target with a model of the target, wherein the second present dataset includes at least a two-dimensional present position value of the target;
   estimating a third present dataset of the target by statistical inference using the first present dataset and the second present dataset, wherein the third present dataset includes at least a three-dimensional present position value of the target; and
   updating the previous dataset of the target to match the third present dataset.

2. The method of claim 1, wherein the statistical inference utilizes an extended Kalman filter.

3. The method of claim 1, wherein the model of the target provides information of three-dimensional spatial distribution of the target at one or more points in time.

4. The method of claim 1, wherein the model of the target is derived from one or more prior images.

5. The method of claim 4, wherein the model of the target is further derived from a surrogate signal indicative of a motion of the target.

6. The method of claim 1, wherein each present dataset of the target further includes a measure of an uncertainty in the respective position value of the target.

7. The method of claim 6, wherein the measure of the uncertainty of the first present dataset is a predicted covariance matrix of a distribution of the target position.

8. The method of claim 7, wherein the predicted covariance matrix is a function of an uncertainty of the state transition model.

9. The method of claim 8, wherein the uncertainty of the state transition model is calculated using a target position tracked in a past time frame.

10. The method of claim 8, wherein the present position value of the target in the first present dataset equals a mean position of the target within a same motion phase of the target in the past 10 seconds to 140 seconds.

11. The method of claim 10 further wherein the uncertainty of the state transition model is estimated to equal a covariance matrix of the target positions within the same motion phase in the past 10 seconds to 140 seconds.

12. The method of claim 1, wherein measuring the second present dataset further comprises processing the two-dimensional image of the target prior to template-matching.

13. The method of claim 1, wherein measuring the second present dataset further includes calculating a template-matching metric.

14. The method of claim 1, wherein the second present dataset further includes a measure of an uncertainty in the two-dimensional present position value of the target.

15. The method of claim 14, wherein the measure of the uncertainty in the two-dimensional present position value of the target is a function of the template-matching metric.

16. The method of claim 1, wherein the target is a tumor.

17. The method of claim 1, wherein the target is a lung tumor.

18. The method of claim 1, wherein the model of the target accounts for the periodic nature of tumor motion.

19. The method of claim 1, wherein predicting the first present dataset of the target further comprises accounting for the periodic nature of tumor motion.

20. The method of claim 1, wherein the body is a human body.

* * * * *